United States Patent [19]
Morris-Natschke et al.

[11] Patent Number: 6,030,960
[45] Date of Patent: Feb. 29, 2000

[54] METHOD OF TREATING HEPATITIS VIRUS INFECTIONS

[75] Inventors: Susan L. Morris-Natschke, Apex; Louis S. Kucera, Pfafftown, both of N.C.

[73] Assignees: Wake Forest University, Winston-Salem; University of North Carolina at Chapel Hill, Chapel Hill, both of N.C.

[21] Appl. No.: 09/102,308

[22] Filed: Jun. 22, 1998

Related U.S. Application Data

[60] Division of application No. 08/465,947, Jun. 6, 1995, Pat. No. 5,770,584, which is a continuation-in-part of application No. 08/074,943, Jun. 10, 1993, abandoned.

[51] Int. Cl.$^7$ .................................................. A61K 31/70
[52] U.S. Cl. ........................ 514/77; 514/43; 514/893; 514/894; 536/26.9; 536/28.6; 536/28.7; 536/28.8; 546/22; 548/112; 558/169; 558/174; 987/102; 987/209; 987/224; 987/233
[58] Field of Search ............................ 514/43, 893, 894, 514/77; 536/26.9, 28.6, 28.7, 28.8; 546/22; 548/112; 558/169, 174; 987/102, 209, 224, 233

[56] References Cited

U.S. PATENT DOCUMENTS

| | | | |
|---|---|---|---|
| 2,086,585 | 7/1937 | Taub et al. | 260/127 |
| 2,087,132 | 7/1937 | Taub et al. | 260/127 |
| 2,108,765 | 2/1938 | Domagk | 167/30 |
| 2,209,383 | 7/1940 | Bock | 8/116 |
| 2,439,969 | 4/1948 | Fourneau | 260/338 |
| 2,445,393 | 7/1948 | Fourneau | 260/338 |
| 2,513,747 | 7/1950 | Sallman et al. | 260/338 |
| 2,606,909 | 8/1952 | Blicke | 260/338 |
| 2,689,790 | 9/1954 | Mowry et al. | 71/2.7 |
| 2,950,253 | 8/1960 | Kling et al. | 252/152 |
| 3,054,678 | 9/1962 | Michener et al. | 99/150 |
| 3,694,473 | 9/1972 | Eibl et al. | 260/403 |
| 4,093,714 | 6/1978 | Tolman et al. | 424/180 |
| 4,096,278 | 6/1978 | Queuille | 424/329 |
| 4,119,714 | 10/1978 | Kny et al. | 424/199 |
| 4,159,988 | 7/1979 | Eibl et al. | 260/340 |
| 4,235,877 | 11/1980 | Fullerton | 424/89 |
| 4,329,302 | 5/1982 | Hanahan et al. | 260/925 |
| 4,426,525 | 1/1984 | Hozumi et al. | 546/22 |
| 4,444,766 | 4/1984 | Bosies et al. | 425/211 |
| 4,471,113 | 9/1984 | Maccoss | 536/29 |
| 4,540,521 | 9/1985 | Garst et al. | 260/459 |
| 4,619,917 | 10/1986 | Lee et al. | 514/77 |
| 4,661,509 | 4/1987 | Gordon et al. | 514/397 |
| 4,816,450 | 3/1989 | Bell et al. | 514/25 |
| 4,826,823 | 5/1989 | Cook et al. | 514/46 |
| 4,835,263 | 5/1989 | Nguyen et al. | 536/27 |
| 4,837,023 | 6/1989 | Eibl | 424/439 |
| 4,841,039 | 6/1989 | Chu et al. | 536/29 |
| 4,880,782 | 11/1989 | Eckstein et al. | 514/45 |
| 5,034,394 | 7/1991 | Daluge | 514/261 |
| 5,138,045 | 8/1992 | Cook et al. | 536/27 |

FOREIGN PATENT DOCUMENTS

| | | |
|---|---|---|
| 0094586 | 11/1983 | European Pat. Off. . |
| 0109255 | 5/1984 | European Pat. Off. . |
| 0146258 | 5/1985 | European Pat. Off. . |
| 0142333 | 6/1985 | European Pat. Off. . |
| 0145303 | 6/1985 | European Pat. Off. . |
| 0252310 | 6/1987 | European Pat. Off. . |
| 0310109 | 4/1989 | European Pat. Off. . |
| 0416401 | 8/1990 | European Pat. Off. . |
| 0434450 | 12/1990 | European Pat. Off. . |
| 0632048 | 6/1994 | European Pat. Off. . |
| 1561630 | 3/1969 | France . |
| 3726945A1 | 10/1989 | Germany . |
| 42-13841 | 8/1967 | Japan . |
| 49-100224 | 9/1974 | Japan . |
| 1029319 | 1/1989 | Japan . |
| 90/15601 | 12/1990 | WIPO . |
| 90/05736 | 3/1991 | WIPO . |
| 91/05568 | 5/1991 | WIPO ..................... A61K 39/395 |
| 91/09602 | 7/1991 | WIPO . |
| 91/18914 | 12/1991 | WIPO . |
| 92/03462 | 3/1992 | WIPO . |
| 93/08807 | 5/1993 | WIPO . |
| 93/16091 | 8/1993 | WIPO . |
| 93/16092 | 8/1993 | WIPO . |
| 93/17020 | 9/1993 | WIPO . |

OTHER PUBLICATIONS

Boldanova, et al., "Protective effect of Phosphatidylcholine–containing Liposomes in Experimental Toxic Hepatitis", *Vopr. Med. Khim*, 32, No. 3 (1986) *Chemical Abstracts,* 105, p. 67, Abstract No. 35587k (1986).

Chen, "Design and Synthesis of Novel Nucleoside Analogs as Potential Antiviral Agents", *Abstract American Assoc. of Pharmaceutical Scientists,* Orlando, FL., (1993).

Crumpton, "Novel Lipid Analogs with Cytostatic and Cytocidal Activity", Submitted to *Anticancer Res.,* vol. 8, No. 6, pp. 1361–1366 (Nov.–Dec. 1988).

Daniel, "Alkyl–Linked Diglygerides Inhibit Protein Kincase C Activation by Diacylglycerols", *Biochemical & Biophysical Res. Comm.,* 151, 291–97 (Feb. 29, 1988).

Dietzfelbinger, "Cytotoxic and Purging Effects of ET–18–OCH3 in Human Malignant Lymphoid Cell Lines in Vitro", Abstract 2472, *Proceedings of the American Assoc. for Cancer Res.,* 31, 416 (Mar. 1990).

Fields, "Human Immunodeficiency Virus Induces Phosphorylation of its Cell Surface Receptor", *Nature,* 333, 278–80 (May 19, 1988).

Harada, "Infection of HTLV–III/LAV in HTLV–I–Carrying Cells MT–2 and MT–4 and Application in a Plaque Assay", *Science,* 229, 563–229 (Aug. 9, 1985).

(List continued on next page.)

*Primary Examiner*—James O. Wilson
*Attorney, Agent, or Firm*—Akin, Gump, Strauss, Hauer & Feld, L.L.P.

[57] ABSTRACT

A method of treating hepatitis virus infection is disclosed. The method comprising administering to a human subject in need of such treatment an effective hepatitis virus-combatting amount of an alkyl lipid or alkyl lipid derivative.

44 Claims, 1 Drawing Sheet

OTHER PUBLICATIONS

Himmelmann, "Studies on the Cross Resistance Pattern of Membrane–Toxic Lipids in Vitro", Abstract 2448, *Proceedings of the American Assoc. for Cancer Res.,* 31, 416 (Mar. 1990).

Hsu, L., et al., "Synthesis of Anti–Restricted Pyrimidine Acyclic Nucleosides", *Journal of Organic Chemistry,* vol. 57, No. 12, pp. 3354–3358 (1992).

Kasnar, B., et al., "Synthesis of 2', 3'–Dideoxy– and 3'–Azido–2', 3'–Dideoxy– Pyridazine Nucleosides as Potential Antiviral Agents", *Nucleosides & Nucleotides,* 13 (1–3), pp. 459–479 (1994).

Korba, "Use of a Standardized Cell Culture Assay to Assess Activities of Nucleoside Analogs Against Hepatitus B Virus Replication", *Antiviral Res.,* 19, 55–70 (1992).

Krugner–higby, et al., "Novel Membrane Interactive Ether Lipid Analogs Inhibit HIV-1 Glycoprotein Interaction with CD4+ Cells", *Abstract from 32nd Interscience Conf on Antimicrobial Agents and Chemotherapy, Anaheim,* 164, (Oct. 11–14, 1992).

Krugner–higby, L., et al., "Membrane–Interactive Phospholipids Inhibit HIV Type 1–Induced Cell Fusion and Surface gp160/gp120 Binding to Monoclonal Antibody", *Aids Research and Human Retroviruses,* vol. 11, No. 6, pp. 705–712, (1995).

Kucera, "Effect of Membrane–Active Ether Lipid (EL) Analogues on Human Immunodefiency Virus Production Measured by Plaque Assay", *Annals of the New York Acad. of Sciences,* 546–548 (Dec. 26, 1990).

Kucera, "Inhibition of HIV–1 Plaque Formation by a Novel Class of Membrane–Active Ether Lipid Analogs", *International Conference on AIDS Abstract No. W.C.O.* 21, Jun. 4–9, 1989, p. 528.

Kucera, "Inhibition of Human Immunodeficiency Virus–1 (HIV–1) by Novel Membrane Interactive Ether Lipids", Abstract No. 2470, *Proceedings of the American Assoc. for Cancer Res.,* 31, 416 (Mar. 1990).

Kucera, "Investigations on Membrane Active Ether Lipid Analogs that Alter Functional Expression of HIV–1 Induces Glycoproteins and Inhibit Pathogenis", *Abstract, Innovations in Theraphy of Human Viral Diseases, Symposium, Research Triangle Park,* 16, (Dec. 6–9, 1992).

Kucera, "Novel Membrane–Interactive Ether Lipid Analogs That Inhibit Infectious HIV–1 Production and Induce Defective Virus Formation", *AIDS Research and Human Retroviruses,* 6, 491–501 (1990).

Kucera, L., et al., "Inhibition of Human Immunodeficiency Virus Envelope Glycoprotein–Mediated Cell Fusion by Synthetic Phospholipid Analogs", *Antiviral Research* (1995).

Kucera, L., et al., "Novel Ether Lipid Analogs of Platelet Activating Factor with Anti–Hepatitis B Virus Activity", *Abstract, ICAAC Orlando,* (1994).

Kucera, L.S., et al., "Activity of Triciribine and Triciribine–5'–Monophosphate Against Human Immunodeficiency Virus Types 1 and 2", *Aids Research and Human Retroviruses,* vol. 9, No. 4, pp. 307–314, (1993).

Marasco, "The Synthesis, Biological Evaluation, and Structure Activity of Amido Phosphocholines and Related Analogs as Anti–HIV–1 Agents", *6th Conf. on AIDS, San Francisco, Abstract,* (Jun. 20–24, 1990).

Marasco, et al., "Synthesis and Biological Activity of Novel Quaternary Ammonium Derivatives of Alkylglycerols as Potent Inhibitors of Protein Kincase C", *Jour. of Med. Chem.,* 3, No. 3, pp. 985–992 (Mar. 1990).

Marasco, et al., "The Synthesis and Biological Testing of Alkyl Glycerols as Potential Inhibitors of Protein Kinase C", *American Assoc. of Pharmaceutical Scientists, Abstract, Orlando FL.,* (1993).

Marasco, Jr., "The Synthesis and Biological Activity of Novel Aklylglycerol Derivatives as Inhibitors of Protein Kinase C Activity, Neoplastic Cell Growth and HIV–1 Infectivity", Dissertation for Ph.D., Univ. of No. Carolina, Chapel Hill 1990.

Marx, "Synthesis and Evaluation of Neoplastic Cell Growth Inhibition of 1–N–Alkylamide Analogues of Glycero–3–phosphocholine", *J. Med. Chem.,* 31, 858–863 (Mar. 28, 1988).

Meyer, "In Vitro Evaluation of Phosphocholine and Quaternary Ammonium Containing Lipids as Novel Anti–HIV Agents", *J. of Med. Chem.,* 34, 1377–83 (1991).

Meyer, "Synthesis and Evaluation of Anti–HIV–1 Ether Lipids", *AAPS Meeting, Atlanta Abstract N. MN*–510, p. S–41, (Oct. 22–25, 1989).

Mitsuya, "Strategies for Antiviral Therapy in AIDS", *Nature,* 325, 773–78 (1987).

Modest, "Antineoplastic and Antiviral Properties of Ether Lipid Analogs", 15th *Intl Cancer Congress, Abstract* (Aug. 16–22, 1990).

Modest, "Combination Chemotherapy Studies with Antitumor and Antiviral Ether Lipid Analogs", Abstract 2471, *Proceedings of the American Assoc. for Cancer Res.,* 31, 416 Abstract 2471 (Mar. 1990).

Modest, "Pharmacological Effects and Anticancer Activity of New Ether Phospholipid Analogs", *The Pharmacological Effect of Lipids, III; The Role of Lipids in Carcinogenesis and Therapy,* (In Press), pp. 330–337 (1989).

Modest, E., et al., "Comparison of Cell Kill Induced by Two Ether Lipids in Combination with Hyperthermia", *Proceddings of the American Association for Cancer Research; Preclinical Pharmacology Experimental Therapeutics,* vol. 31, pp. 416, Abstract 2467, (Mar. 1990).

Morrey, "Effects of Zidovudine on Friend Virus Complex Infection in Rfv–3r/s Genotype–Containing Mice Used as a Model for HIV Infection", *J. of Acquired Immune Deficiency Syndromes.*

Morris–natschke, "Synthesis of Sulfur Analogues of Alkyl Lysophospholipid and Neoplastic Cell Growth Inhibitory Properties", *J. of Med. Chem.,* 29, 2114–17 (1986).

Nara, "Simple, Rapid, Quantitative, Syncytium–Forming Microassay for the Detection of Human Immunodeficiency Virus Neutralizing Antibody", *Aids Res. and Human Retroviruses,* 3, 283–301 (1987).

Noseda, "In Vitro Antiproliferative Activity of Combinations of Ether Lipid Analogues and DNA–interactive Agents Against Human Tumor Cells", *Journal of Cancer Research,* 48, 1788–1791 (Apr. 1988).

Noseda, "Neoplastic Cell Inhibition with New Ether Lipid Analogs", *Lipids,* 22, 878–883 (Nov. 1987).

Ostertag, "Induction of Endogenous Virus and of Thymidine Kinase by Bromodeoxyuridine in Cell Cultures Transformed by Friend Virus", *Proc. Nat. Acad. Sci. USA,* 71, 4980–85 (Dec. 1974).

Pacheco, "Mechanisms of Toxicity of Hepsulfam in Human Tumor Cell Lines", Abstract 2446, *Proceedings of the American Assoc. for Cancer Res.,* 31, 416 (Mar. 1990).

Piantadosi, "Synthesis and Evaluation of Novel Ether Lipid Nucleoside Conjugates for Anti– HIV–1 Activity", *J. Med. Chem.,* 34, 1408–1414, (1991).

Sarin, et al., "Effects of a Novel Compound (AL 721) on HTLV–III Infectivity in Vitro", *New England J. of Med.,* 313, 1289–90 (Nov. 14, 1985).

Small, "Characterization of Cells Sensitive and Resistant to ET–18–OCH3", Abstract 2447, *Proceedings of the American Assoc. for Cancer Res.,* 31, 416 (Mar. 1990).

Swayze, E.E., et al., "Synthesis of 1–(2–Aminopropyl) Benzimidazoles, Structurally Related to the Tibo Derivative R82150, With Activity Against Human Immunodeficiency Virus", *Bioorganic & Medical Chemistry Letters,* vol. 3, No. 4, pp. 543–546 91993).

Thompson, J., et al., "Phospholipid Analog Inhibition of Human Immunodeficiency Virus Envelope Glycoprotein––Mediated Cell Fusion", *Abstracts of the 2nd National Conference on Human Retroviruses, Session* 18, (1995).

Yanagawa, "Spontaneous Formation of Superhelical Strands", *J. Am. Chem. Soc.,* 111, 4567–70 (1989).

Yarchoan, "Therapeutic Strategies in the Treatment of AIDS", *Annual Reports in Medicinal Chemistry,* 253–263 (1988).

FIG. 1

METHOD OF TREATING HEPATITIS VIRUS INFECTIONS

This is a divisional application of U.S. Ser. No. 08/465,947 filed Jun. 6, 1995, now U.S. Pat. No. 5,770,584 which is a continuation-in-part application of U.S. patent application Ser. No. 08/074,943, filed Jun. 10, 1993, now abandoned, which is incorporated herein by reference.

FIELD OF THE INVENTION

This invention relates generally to the treatment of hepatitis virus infections, and more specifically to the treatment of hepatitis virus infections with alkyl lipids and alkyl lipid derivatives.

BACKGROUND OF THE INVENTION

The human hepatitis B virus (HBV) is one of a family of hepadnaviruses that cause acute and chronic liver disease, including liver cancer. The virus is found in the body fluids of infected persons. Recognized risk factors for infection include blood transfusion, sexual contact, hemodialysis, shared intravenous needles, acupuncture, tissue transplantation and the like.

The virus makes three antigenic proteins during multiplication in liver cells: hepatitis B surface antigen (HBsAg), hepatitis B e antigen (HBeAg) and hepatitis B core antigen (HBcAg). These three virus antigenic proteins are important as markers for determining virus infection, as antibodies against the virus infection are made is response to these virus proteins in the blood.

Currently, there are no specific antiviral agents to treat acute or chronic persistent hepatitis. An HBV vaccine is available to prevent infection, and hyperimmune gamma globulin is available for temporary prophylaxis against developing HBV infection in persons at risk. Clearly specific antiviral agents are needed for treatment and control of HBV infections in humans. Alkyl lipids and derivatives are known point biologic agents that effectively inhibit tumor cell growth and HIV-1 multiplication. See, Marx et al., *J. Med. Chem.* 31:858–863 (1988), and Kucera et al., *AIDS Res. Human Retroviruses* 6:491–501 (1990). The major sites of action of the;e agents involves the plasma membrane of tumor cells, of HIV-1 infected cells and protein kinase C.

Based on the foregoing, it is an object of the present invention to provide a new treatment method for combatting the effects of hepatitis virus infections, and for inhibiting hepatitis; virus DNA and virion production.

It is a second object of the present invention to provide compositions for carrying out the same.

SUMMARY OF THE INVENTION

These and other objects are satisfied by the present invention, which as a first aspect provides a method of treating hepatitis virus infection in a human subject in need of such treatment. The method comprises administering to the human subject, in an amount effective to inhibit hepatitis virus DNA replication and virion production, a compound of Formula I:

(I)

wherein
Y is S, O, NCH, NH$_3$, NHC(O), or NCH$_3$C(O);
R$_1$ is unbranched or branched, saturated or unsaturated C1–C20 alkyl, alkenyl, or alkynyl;
X is a covalent bond or methylene optionally substituted with hydroxyl, C1–C20 alkyl, C1–C20 alkoxy, C1–C10 alkylthio or C1–C20 alkylamido;
and D is selected from the group consisting of moieties of Formula V or Formula VI;
wherein Formula V is $$-(PO_4)^- - E \qquad\qquad (V)$$

wherein E is selected from the group consisting of:

wherein J is C1–C4 alkyl optionally substituted one to three times with methyl or ethyl; and R$_2$, R$_3$, and R$_4$ are independently selected from the group consisting of H and C1–C3 alkyl; and
a nucleic acid base conjugate of the Formula VII (VII)

wherein the base is selected from the group consisting of thymine, adenine, cytosine, guanine, hypoxanthine, uracil, 2'-3'-dideoxy-3'-thiacytidine, and 2-aminoadenine; A is H, OH, fluorine; or N$_3$; and B is H or fluorine, or A and B together form a covalent bond;
and wherein Formula VI is $$-N^+(R_5)(R_6)-J-W\ Z^- \qquad\qquad (VI)$$

wherein
R$_5$ and R$_6$ are independently selected from the group consisting of H and C1–C3 alkyl;
J is as defined above;
W is —OH, or —SH; and
Z$^-$ is an anion;
or a pharmaceutical salt thereof.

In particular, the method of the present invention comprises administering a compound of Formula I to a human subject in an amount effective to inhibit Hepatitis A virus, Hepatitis B virus, Hepatitis C virus, Hepatitis D virus or Hepatitis E virus.

A second aspect of the present invention is a method of inhibiting the production of a hepatitis virus-induced antigen. The hepatitis virus may be Hepatitis A virus, Hepatitis B virus, Hepatitis C virus, Hepatitis D virus or Hepatitis E virus. The antigen may be Hepatitis B virus core antigen or e antigen. The method comprises administering to a human subject an effective antigen-production limiting amount of a compound of Formula I.

A third aspect of the present invention is a method of treating hepatitis virus infection in a human subject in need of such treatment. The method comprises administering to the human subject in an amount effective to inhibit hepatitis virus DNA replication and virion production a compound of Formula II:

(II)

wherein

Y is S, O, NH, $NCH_3$, NHC(O), or $NCH_3C(O)$;

$R_1$ is unbranched. or branched, saturated or unsaturated C1–C20 alkyl, alkenyl, or alkynyl;

X is a covalent bond or methylene optionally substituted with hydroxyl, C1–C20 alkyl, C1–C20 alkoxy, C1–C20 alkylthio or C1–C20 alkylamido;

J is C1–C4 alkyl optionally substituted one to three times with methyl or ethyl; and $R_2$, $R_3$, and $R_4$ are independently selected from the group consisting of H and C1–C3 alkyl; or a pharmaceutical salt thereof. In particular, the method of the present invention comprises administering a compound of Formula II to a human subject in an amount effective to inhibit Hepatitis A virus, Hepatitis B virus, Hepatitis C virus, Hepatitis D virus or Hepatitis E virus.

A fourth aspect of the present invention is a method of inhibiting the production of a hepatitis virus-induced antigen. These hepatitis virus-induced antigens are antigens that are produced as a result of the hepatitis virus infection as opposed to cellular antigens. The hepatitis virus may be Hepatitis A virus, Hepatitis B virus, Hepatitis C virus, Hepatitis D virus or Hepatitis E virus. The antigen may be Hepatitis B virus core antigen or e antigen. The method comprises administering to a human subject an effective antigen-production inhibiting amount of a compound of Formula II.

A fifth aspect of the present invention is a method of treating hepatitis virus infection in a human subject in need of such treatment comprising administering to the human subject a compound of Formula III (III)

wherein

Y is S, O, NH, $NCH_3$, NHC(O), or $NCH_3C(O)$;

$R_1$ is an unbranched or branched, saturated or unsaturated C1–C20 alkyl, alkenyl, or alkynyl;

X is a covalent bond or methylene optionally substituted 1 or 2 times with hydroxyl, C1–C20 alkyl, C1–C20 alkoxy, C1–C20 alkylthio or C1–C20 alkylamido;

J is C1–C4 alkyl optionally substituted one to three times with methyl or ethyl;

$R_2$ and $R_3$ are independently selected from the group consisting of H and C1–C3 alkyl;

W is —OH, or —SH; and $Z^-$ is an anion.

The compound is administered in an amount effective to combat the hepatitis virus infection. In particular, the method of the present invention comprises administering a compound of Formula III to a human subject in an amount effective to inhibit Hepatitis A virus, Hepatitis B virus, Hepatitis C virus, Hepatitis D virus or Hepatitis E virus.

A sixth aspect of the present invention is a method of inhibiting the production of a hepatitis virus-induced antigen. The hepatitis virus may be Hepatitis A virus, Hepatitis B virus, Hepatitis C virus, Hepatitis D virus or Hepatitis E virus. The antigen may be Hepatitis B virus core antigen or e antigen. The method comprises administering to a human subject an effective antigen-production limiting amount of a compound of Formula III.

A seventh aspect of the present invention is a method of treating hepatitis virus infection in a human subject in need of such treatment comprising administering to the human subject a compound of Formula IV.

(IV)

wherein

Y is S, O, NH, $NCH_3$, NHC(O), or $NCH_3C(O)$;

$R_1$ is an unbranched or branched, saturated or unsaturated C1–C20 alkyl, alkenyl, or alkynyl, X is a covalent bond or methylene optionally substituted with hydroxyl, C1–C20 alkyl, C1–C20 alkoxy, C1–C20 alkylthio or C1–C20 alkylamido;

The base is selected from the group consisting of thymine, adenine, cytosine, guanine, hypoxanthine, uracil, 2'-3'-dideoxy-3'-thiacytidine, and 2-aminoadenine;

A is H, OH, fluorine, or $N_3$; and B is H or flourine, or A and B together form a covalent bond. In particular, the method of the present invention comprises administering a compound of Formula IV to a human subject in an amount effective to inhibit Hepatitis A virus, Hepatitis B virus, Hepatitis C virus, Hepatitis D virus or Hepatitis E virus.

An eighth aspect of the present invention is a method of inhibiting the production of a hepatitis virus-induced antigen. The hepatitis virus may be Hepatitis A virus, Hepatitis B virus, Hepatitis C virus, Hepatitis D virus or Hepatitis E virus. The antigen may be Hepatitis B virus core antigen or e antigen. The method comprises administering to a human subject an effective antigen-production inhibiting amount of a compound of Formula IV.

A ninth aspect of the present invention is the use of an alkyl lipid or alkyl lipid derivative of formulas I, II, III, or IV given above for the preparation of a medicament combatting hepatitis virus infection and inhibiting hepatitis virus virion production. The hepatitis virus may be Hepatitis A virus, Hepatitis B virus, Hepatitis C virus, Hepatitis D virus or Hepatitis E virus.

DETAILED DESCRIPTION OF THE INVENTION

As used herein, the term "alkyl" is intended to refer to an unbranched or branched alkyl group comprising carbon atoms, such as methyl, ethyl, propyl, isopropyl, n-butyl, tert-butyl, hexyl, and octyl. This definition also applies to an alkyl moiety in the alkoyy group. Examples of alkoxy groups are methoxy, ethoxy, propoxy, and isohexoxy. Similarly, the term "alkenyl" means an unbranched or branched alkenyl group comprising carbon atoms and having at least one double bond, such as ethenyl, propenyl, isopropenyl, n-butenyl, tert-butenyl, hexenyl, and octenyl. The term "alkynyl" means an unbranched or branched alkynyl group (comprising carbon atoms and having at least one triple bond.

The term "pharmaceutical salt" refers to a salt that retains the desired biological activity of the parent compound and does not impart undesired toxicological effects thereto. Examples of such salts are (a) salts formed with cations such as sodium, potassium, $NH_4^+$, magnesium, calcium polyamines, such as spermine, and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The term "amphipathic" refers to a compound having both a polar hydrophilic end and a non-polar hydrophobic end. The term "amphoteric" refers to a compound that has both a negative and positive charge within the same compound.

The present invention is directed to the use of alkyl lipids and quaternary amine containing ether lipid derivatives and therapeutic compositions in the therapy of hepatitis virus infections. Such infections may be by Hepatitis A virus, Hepatitis B virus, Hepatitis C virus, Hepatitis D virus, or Hepatitis E virus. In particular, the present invention is directed to the treatment of Hepatitis B virus infection. It has been discovered that the compounds of Formulas I, II, III and IV above can be used to treat hepatitis virus infection and virion production in human subjects in need of such treatment, as viral hepatitis is combatted by administration of alkyl lipids or derivatives thereof to such human subjects. While the inventors do not wish to be bound by any mechanism that explains how these compounds combat hepatitis virus infection, it has also been observed that production of Hepatitis B virus core and e antigens is inhibited by treatment with these compounds. It is believed that the site of action most likely involves inhibition of Hepatitis B virus DNA and post-transcriptional protein synthesis and replication at cell membranes.

A first aspect of the invention is a method of inhibiting hepatitis virus DNA and hepatitis virus antigen virion production using a compound of Formula I, wherein $R_1$, Y, X, and D) are defined as stated above, or a pharmaceutical salt thereof. The compounds of Formula I are amphipathic moieties having a short alkyl backbone (represented by C—X—C in Formula I), a hydrophobic end represented by $R_1$ linked to one end of the alkyl backbone by the functional group Y, and a hydrophilic end D linked to the other end of the short alkyl chain. D is generally amphoteric and is; preferably a phospho-ammonium or -nucleic acid-base complex (Formula V) or an alkyl ammonium-anion complex (Formula VI).

Formulas II, III, and IV represent preferred embodiments of the compounds of Formula I. The individual components of each are described in detail below.

In Formula II, as described above, $R_1$ is a lipophilic moiety; the lipophilicity of $R_1$ allows the compounds of Formula II to bind with the cell membrane of a cell infected with the hepatitis virus to provide an anchor thereto. $R_1$ can be an unbranched or branched, saturated or unsaturated C1–C20 alkyl, alkenyl, or alkynyl. Preferably, $R_1$ is an unbranched saturated or unsaturated (C1–C20)alkyl, i.e., a C1–C20 alkyl group. Most preferably, $R_1$ is a lipophilic moiety comprising an unbranched. saturated or unsaturated C14–C18 alkyl group.

In compounds of Formula II, Y is a functional group that links the lipophilic moiety $R_1$ and the short alkyl backbone of the compound. Y should be a functional group, such as S, O, NH, $NCH_3$, NHC(O), or $NCH_3C(O)$, that is able to withstand the hydrolytic activity of cellular lipases. Preferably, Y is S or NHC(O).

The alkyl backbone includes a constituent X which can be a covalent bond between the carbon atoms at either end of the backbone or a methylene optionally substituted with hydroxyl, C1–C20 alkyl, C1–C20 alkoxy, C1–C20 alkylthio or C1–C20 alkylamido. Preferably, X is a covalent bond or a methylene substituted with a hydroxyl or C1–C4 alkoxy; more preferably, X is methylene substituted with hydroxyl, methoxy or ethoxy. Most preferably, X is ethoxy.

The polar hydrophilic end of the amphipathic compounds of Formula II comprises an amphoteric Lmmonium phosplhoalkyl group in which the phosphate moiety carries the negative charge and the ammonium moiety carries the positive charge. In the ammoni .m phosphoalkyl group, J is C1–C4 alkyl optionally substituted one to three times with methyl or ethyl, and $R_2$, $R_3$, and $R_4$ are independently selected from the group consisting of hydrogen and C1–C3 alkyl. It is preferred that J be unsubstituted ethylene. It is also preferred that $R_2$, $R_3$, and $R_4$ are each methyl. It is particularly preferred that J is unsubstituted ethylene and $R_2$, $R_3$, and $R_4$ are each methyl.

Exemplary compounds of Formula II include rac-3-octadecanamido-2-ethyoxy-1-propylphosphocholine (hereinafter CP-51), rac-3-hexadecanamido-2-ethoxy-1-propylphosphocholine (hereinafter CP-49), 2-hexadecylthio-1-ethylphosphocholine (hereinafter CP-9), and rac-3-octadecyloxy-2-hydroxy-1-propyl phosphocholine (hereinafter lyso PAF).

Compounds of Formula II can be synthesized according to known procedures. See, e.g., *Lipids* 22 (11), 775–980 (1987); exemplary synthetic procedures are set forth below in the Examples. Among numerous noteworthy subsequent developments are the sulfur-containing phospholipids described in U.S. Pat. No. 4,444,766 to Bosies et al., the phosphoric acid ester derivatives of 1,3-dioxy propane disclosed in U.S. Pat. No. 4,426,525 to Hozumi et al., the cyclammonium salts disclosed (as platelet activating factor inhibitors) in U.S. Pat. No. 4,619,917 to Lee et al., and the lipoidal amine disclosed by J. Wolff et al., *Cancer Immunol. Immunother.* 12:97–98 (1982).

Another aspect of tire invention is the inhibition of hepatitis virus DNA and hepatitis virus antigen virion production using an alkyl lipid of Formula III, wherein $R_1$, Y, X, J, $R_2$, $R_3$, W and Z are defined as stated above, or using a pharmaceutical salt thereof. Compounds of Formula III are amphipathic moieties having a hydrophobic end ($R_1$) linked to a hydrophilic alkyl ammonium-anion complex by a short alkyL. backbone, wherein the polar, hydrophilic end is an inverse choline (e.g., N,N-dimethyl-β-hydroxyethyl ammonium).

$R_1$ can be an unbianched or branched, saturated or unsaturated C1–C20 alkyl, alkenyl, or alkynyl. As with the compounds of Formulas I and II, $R_1$ is a lipophilic moiety which binds with the cell membrane of infected cells to provide an anchor thereto. Preferably, $R_1$ is unbranched saturated or unsaturated C1–C20 alkyl. More preferably, $R_1$ is unbranched saturated or unsaturated C14–C18 alkyl.

As with the compounds of Formulas I and II, in compounds of Formula III Y is a functional group that links the lipophilic moiety $R_1$ and the short alkyl backbone of the compound. Y should be a functional group, such as S, O, NH, $NCH_3$, NHC(O), or $NCH_3C(O)$, that is able to withstand the hydrolytic activity of cellular lipases. Preferably, Y is S or NHC(O).

The alkyl backbone of Formula III includes a constituent X which can be a covalent bond between the carbon atoms at either end of the backbone or a methylene optionally substituted with hydroxyl, C1–C20 alkyl, C1–C20 alkoxy, C1–C20 alkylthio or C1–C20 alkylamido. Preferably, X is a covalent bond or a methylene substituted with a hydroxyl or C1–C4 alkoxy; more preferably, X is methylene substituted with hydroxyl, methoxy or ethoxy.

The polar hydrophilic end of the amphipathic compounds of Formula III comprises an alkyl ammonium-anion complex wherein the anion, Z, carries the negative charge and the ammonium moiety carries the positive charge. In the alkyl ammonium moiety, J is C1–C4 alkyl optionally substituted one to three times with methyl or ethyl, W is, OH or SH, and $R_2$ and $R_3$ are independently selected from the group consisting of hydrogen and C1–C3 alkyl. It is preferred that J is unsubstituted ethylene and W is OH. It is also preferred that $R_2$ and $R_3$ are each methyl. It is more preferred that J is unsubstituted ethylene, W is OH, and $R_2$ and $R_3$ are each methyl.

An exemplary compound of Formula III is N-[rac-3-(hexadecylthio)-2-methoxy-1-propyl]-N,N-dimethyl-N-(2-hydroxyethyl) ammonium bromide (hereinafter CP-7).

In addition to CP-7, which is synthesized according to Example 5 below, compounds of Formula III can be synthesized by following the teachings of Example 5 in combination with procedures known to those skilled in the art.

An additional aspect of the invention is a method of inhibiting hepatitis virus DNA and hepatitis virus antigen virion production using a compound of Formula IV, wherein $R_1$, Y, X, A, B and Base are defined as stated above, or using a pharmaceutical salt thereof. Compounds of Formula IV are amphipathic moieties wherein the polar hydrophilic end is a phospho-nucleic acid conjugate.

In the compounds of Formula IV, the non-polar hydrophobic end is $R_1$, which can be an unbranched or branched, saturated or unsaturated C1–C20 alkyl, alkenyl, or alkynyl group. As for the compounds of Formulas I, II and III, $R_1$ is a lipophilic moiety which binds with the cell membrane of an hepatitis virus infected cell to provide an anchor for the compound thereto. Preferably, $R_1$ is an unbranched saturated or unsaturated C1–C20 alkyl group. More preferably, $R_1$ is an unbranched saturated or unsaturated C14–C18 alkyl group.

As with the compounds of Formulas I, II and III, in compounds of Formula IV Y is a functional group that links the lipophilic moiety $R_1$ and the short alkyl backbone of the compound. Y should be a functional group, such as S, O, NH, $NCH_3$, NHC(O), or $NCH_3C(O)$, that is able to withstand the hydrolytic activity of cellular lipase. Preferably, Y is S or NHC(O).

The alkyl backbone of Formula IV includes a constituent X which can be a covalent bond between the carbon atoms at either end of the backbone or a methylene optionally substituted with hydroxyl, C1–C20 alkyl, C1–C20 alkoxy, C1–C20 alkylthio or C1–C20 alkylamido. Preferably, X is a covalent bond or a methylene substituted with a hydroxyl or C1–C4 alkoxy; more preferably, X is methylene substituted with hydroxyl, methoxy or ethoxy.

In the amphipathic compounds of Formula IV, the polar hydrophilic end of the compound comprises a phospho-nucleic acid conjugate. Many of the nucleic acid moieties that are suitable for use with the present invention are moieties that have shown anti-retroviral activity on other viruses by a different mechanism than that postulated herein, and thus are attached to the compounds of Formula IV to provide an additional impediment to viral activity. The nucleotide base is selected from the group consisting of thymine, adenine, cytosine, guanine, hypoxanthine, uracil, 2'-3'-dideoxy-3'-thiacytidine, and 2-aminoadenine. Thymine is a preferred base. A is hydrogen, fluorine or $N_3$, and B is hydrogen or fluorine, or A and B together form a covalent bond (i.e., there is a double bond between A and B). It is preferred that A is hydrogen or $N_3$ and B is hydrogen. A particularly preferred nucleotide moiety is 3'-azido-3'deoxythymidine (AZT) or 2'-3'-dideoxy-3'-cytidine.

An exemplary compound of Formula IV is 3'-Azido-3'-deoxy-5'-(rac-3-dodecyloxy-2-decyloxy-1-propyl) phosphothymidine (hereinafter CP-126).

CP-126 and other compounds of Formula IV can be synthesized according to the method of PCT Application No. WO 91/19726 to Piantadosi et al., the entirety of which is herein incorporated by reference, and by the methods set forth in Example 4 below.

Experimentation has demonstrated the efficacy of the compounds of Formulas I, II, III, and IV in combatting hepatitis virus infection (see below Examples 6 and 7). For example, both compounds CP-49 and CP-51 substantially inhibited the levels of HBV virion DNA and intracellular HBV-DNA replication intermediate (RI) to levels comparable to, or greater than, that observed following evaluation of an internal positive control compound 2', 3'-dideoxycytidine (ddC). Compounds CP-7, CP-9 and CP-126 were moderately inhibitory of HBV replication. The levels of virion DNA and intracellular HBV DNA replication intermediates were reduced to amounts comparable to, but slightly less than, for ddC. In addition, CP-51 has been demonstrated to inhibit the production of the HBV antigens core antigen and e antigen. This result suggests that the mechanism of action of the compounds involves suppression of nucleocapsid and HBV pregenomic RNA packaging to form new HBV particles.

In the manufacture of a medicament according to the invention, hereinafter referred to as a "formulation," the compounds of Formulas I, II, III and IV are typically admixed with, among other things, an acceptable carrier.

The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components.

The formulations cf the invention include those suitable for oral, rectal, topical, intrathecal, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like.

Capsules, both hard and soft, are filled with compositions of these amino-amide active ingredients in combination with suitable diluents and excipients, for example, edible oils, talc, calcium carbonate and the like, and also calcium stearate.

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Liquid preparations for oral administration are prepared in water or aqueous vehicles which advantageously contain suspending agents, for example, methylcellulose, acacia, polyvinylpyrrolidone, polyvinyl alcohol and the like.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the, present invention suitable for parenteral administration conveniently comprise sterile aqueous preparations of the active compound, which preparations are preferably isotonic with the blood of the intended recipient. These preparations are preferably administered intravenously, although administration may also be effected by means of subcutaneous, intramuscular, intrathecal, or intradermal injection. The formulation should be sufficiently fluid that easy syringe ability exists. Such preparations may conveniently be prepared by admixing the compound with water or a glycine buffer and rendering the resulting solution sterile and isotonic with the blood. Such preparations should be stable under the conditions of manufacture and storage, and ordinarily contain in addition to the basic solvent or suspending liquid, preservatives in the nature of bacteriostatic and fungistitic agents, for example, parabens, chlorobutanol, benzyl alcohol, phenol, thimerosal, and the like. In many cases, it is preferable to include osmotically active agents, for example, sugars or sodium chloride in isotonic concentrations. Injectable formulations according to the invention generally contain from 0.1 to 5% w/v of active compound and are administered at a rate of 0.1 ml/min/kg.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, for example, Pharmaceutical Research 3 (6), 318, (1986)) and typically take the form of an optionally buffered aqueous solution of the active compound. Suitable formulations comprise citrate or bistris buffer (pH 6) or ethanol/water and contain from 0.1 to 0.2M active ingredient.

The compounds of Formulas I, II, III and IV are administered in an amount sufficient to inhibit hepatitis virus DNA and virion production. The dose can vary depending on the compound selected for administration, the human subject, the route of administration, and other factors. Preferably, the compound is administered in an amount of at least 0.1 mg/kg, 1 mg/kg, 10 mg/kg or more, and is adminstered in an amount no greater than 0.1 g/kg, 0.01 g/kg, 0.001 g/kg, or less.

The invention is illustrated in greater detail in the following non-limiting examples. In the Examples, "mg" means milligrams, "pg" means picograms, "nM" means nanomolar, "$\mu$M" means micromolar, "ml" means milliliters, "°C." means degrees Celsius, "DMF" means dimethylformamide, "nmol" means moles, "mmol" means millimoles, and "Kg" means Kilograms.

EXAMPLE 1

Preparation of (±)-3-N-Octadecanamido-2-ethoxypropyl-1-phosphocholine

A. Preparation of (+)-3-Octadecanamido-1,2-propanediol

To a mechanically stirred solution of 3-amino-1,2-propanediol (32 g, 0.35 mol) in 100 mL of pyridine and 250 mL of DMF was added a solution of stearoyl chloride (100.0 g, 0.33 mol) in 150 mL of DMF. After stirring for 1 h, precipitation occurred and an additional 100 mL of DMF was added. After 2 h, the gelatinous mass was filtered, washed with water, and air dried. The solid was recrystallized successively from EtOH, isopropanol, and chloroform to give 74 g (63%) as a white powder (mp 111.5–113.5° C.). $^1$H-NMR: 0.86 (t, 3H, CH$_3$), 1.25 (broad m, 28H, (CH$_2$)$_{14}$), 1.55 (m, 2H, NHCOCH$_2$C$\underline{H}_2$), 2.20 (t, 2H NHCOC$\underline{H}_2$), 3.4 (m, 2H, C$\underline{H}_2$NH), 3.55 (d, 2H, C$\underline{H}_2$OH). 3.75 (m, 1H, CH), 5.8 (m, 1H, NH).

B. Preparation of (+)-3-N-Octadecanamido-1-triphenylmethory-2-propanol

Trityl chloride (40g, 0.11 mol) was added to a stirring solution of (+)-3-octadecanamido-1,2-propinediol (35 g, 0.1 mol) in 250 mL of pyridine. The reaction mixture was heated to 45–50° C. for 10 h. After removing the pyridine under reduced pressure, the residue was diluted with 100 mL of water and extracted three times with 100 mL of chloroform. The combined extracts were washed with 50 mL each of cold, 5% HCl and saturated NaCl, dried over sodium sulfate, filtered, and evaporated to dryness. The crude residue was recrystallized two times from hexane, thereby giving 43 g (72%, mp 86–88° C.) of the trityl ether. $^1$H-NMR: 0.90 (t, 3H, CH$_3$), 1.25 (broad m, 28H, (CH$_2$)$_{14}$), 1.55 (m, 2H, NHCOCH$_2$C$\underline{H}_2$), 2.10 (t, 2H, NHCOC$\underline{H}_2$), 3.15 (overlapping m, 3H, C$\underline{H}_2$NH, CH$\underline{H}'$OTr), 3.5 (m, 1H, (CH $\underline{H}'$OTr), 3.85 (m, 1H, CH), 5.6 (m, 1H, NH), 7.35 (m, 15H, aromatic H).

C. Preparation of (+)-3-N-Octadecanamido-2-ethoxy-1-triphenylmethoxypropane

A solution of (+)-3-N-Octadecanamido-1-triphenylmethory-2-propanol (28 g, 0.045 mol) in 100 mL THF was added to a slurry of 80% NaH (1.8 g, 0.05 mol) in 10 mL THF. Aftei stirring for 30 min at room temperature, ethyl iodide (4 mL, 7.8 g, 0.05 mol) was added and the reaction mixture heated to 50° C. for 2 h. An additional 0.3 g NaH and 2 mL of EtI was added and heating continued for 2 h. After cooling, waler was added slowly to decompose any residual NaH. Diethyl ether (100 mL) was added and the layers separated. The aqueous layer was reextracted with ether and the organic extracts combined, washed with brine, and dried over sodium sulfate. The crude product was dissolved in hot hexane and a small amount of insoluble material filtered and discarded. After cooling at 0° C., 21.7 g (78%, mp 58–61° C.) of product was obtained. Chromatography of silica gel using hexane: $^1$H-NMR: 0.80 (t,3H, CH$_3$), 1.25 (broad m, 31H, (CH$_2$)$_{14}$, OCH$_2$C$\underline{H}_3$), 1.55 (m, 2H, NHCOCH$_2$C$\underline{H}_2$), 2.15 (t, 2H, NHCOC$\underline{H}_2$), 3.1.–3.7 (m, 7H, C$\underline{H}_2$N, CHC$\underline{H}_2$OH, OC$\underline{H}_2$CH$_3$), 5.7 (m, 1H, NH), 7.25 (m, 15H, aromatic H).

D. Preparation of (+)-3-N-Octadecanamido-2-ethoxy-1-propanol p-Toluenesulfonic acid (1 g, 0.005 mol) was added to a solution of (+)-3-N-Octadecanamido-2-ethoxy-1-triphenylmethoxypropane (21.7 g, 0.035 mol) in 100 mL of methylene chloride and 20 mL of methanol. The solution was stirred for 8 h at room temperature. Saturated sodium bicarbonate was added and stirred for 0.5 h. The layers were separated and the organic fraction washed with brine. After drying over sodium sulfate, the solution was concentrated in vacuo. Crude product was obtained by precipitation from hexane. Chromatography on silica gel with a gradient of methylene chloride:methanol (100:0 to 95:5) gave 9 g (69%, mp 79–80° C.) as a white solid. $^1$H-NMR: 0.85 (t, 3H, CH$_3$), 1.25 (broad m, 31H, (CH$_2$)$_{14}$, OCH$_2$C$\underline{H}_3$), 1.55 (m, 2H, NHCOCH$_2$C$\underline{H}_2$), 2.20 (t, 2H, NHCOC$\underline{H}_2$), 3.3–3.9 (overlapping m, 7H, C$\underline{H}_2$N, CHC$\underline{H}_2$OH, OC$\underline{H}_2$CH$_3$), 5.9 (m, 1H, NH).

D. Preparation of (+)-3-N-Octadecanamido-2-ethoxypropyl-1-phosphocholine (CP-51)

To a cooled (ice bath) stirring solution of (+)-3-N-Octadecanarnido-2-ethoxy-1-propanol (1.0 g, 0.0026 mol) and triethylamine (0.29 g, 0.0029 mol) in 40 mL of dry benzene was added 2-chloro-2-oxo-1,3,2-dioxophospholane (0.41 g, 0.0029 mol) in 4 mL benzene. The reaction mixture was stirred at room temperature for 4 h. The precipitate was filtered and washed with benzene. The filtrate was concentrated ard the intermediate phosphotriester was used without further purification. The solid was transferred to a dry pressure flask containing 40 mL of dry acetonitrile and cooled in a dry ice/acetone bath. Trimethylamine (3 mL) was condensed and added to the reaction vessel. The flask was sealed and the reaction mixture heated to 65° C. overnight. A white solid formed upon cooling and was filtered and precipitated from chloroform:acetone (1:10). Chromatography on silica gel eluting with chloroform:methanol:ammonium hydroxide (70:35:2 to 70:3:5:5) gave pure product (0.6 g, 42%, hygroscopic solid, decomposes 245° C.) which was precipitated again from chloroform:acetone. $^1$H-NMR: 0.85 (t, 3H, CH$_3$), 1.15 (t, 3H, OCH$_2$C$\underline{H}_3$), 1.25 (broad m, 28H, (CH$_2$)$_{14}$), 1.60 (m, 2H, NHCOCH$_2$C$\underline{H}_2$), 2.18 (t, 2H, NHCO C$\underline{H}_2$), 3.35 (s, 9H, N(CH$_3$)$_3$), 3.3–3.7 (overlapping m, 6H, C$\underline{H}_2$N(CH$_3$)$_3$, C$\underline{H}_2$NH, OC$\underline{H}_2$CH$_3$), 3.7–4.1 (m, 3H, CH$_2$OP), 4.35 (m, 2H, POCH$_2$), 7.1 (m, 1H, NH). Elemental analysis C$_{28}$H$_{59}$N$_2$O$_6$P•H$_2$O

EXAMPLE 2

Preparation of (±)-3-N-Hexadecanamido-2-ethoxypropyl-1-phosphocholine (CP-49)

This compound was prepared by the same procedure set forth in Examples 1 with the substitution of palmitoyl chloride for stearoyl chloride in the reaction described in section A above. Alternatively, this compound was prepared using the following method. To a solution of alcohol (0.2 grams, 0.5 mmol) in anhydrous diethyl ether:THF (2:1, 12 mL) at 0° C. was added dry pyridine (0.6 mL, 7 mmol) followed by 2-bromoethyl dichlorophosphate (0.3 mL, 1.9 mmol). The reaction mixture was warmed to room temperature and heated at a gentle reflux for 4 hours. The heat was removed, water (3 mL) was added and the reaction mixture stirred for 0.5 hours. Solvent was removed and the residue dissolved in chloroform:methanol (2:1). This solution was extracted with water, dried over sodium sulfate, and the solvent removed on a rotary evaporator. Column chromatography on silica gel with a gradient of chloroform methanol (100:0 to 3:1) was used to purify the bromoethyl phosphate (0.15 grams, 52%, R$_f$-0.3 in chloroform:methanol 4:1). $^1$H-NMR: 0.85 (t, 3H, CH$_3$), 1.15 (t, 3H, OCH$_2$C$\underline{H}_3$), 1.25 (broad m, 28H, (CH$_2$)$_{14}$), 1.6 (m, 2H, NHCOCH$_2$C$\underline{H}_2$), 2.28 (t, 2H, NHCOC$\underline{H}_2$), 3.3–4.0 (overlapping m, 9H, C$\underline{H}_2$Br, C$\underline{H}_2$NH, OC$\underline{H}_2$CH$_3$, C$\underline{H}$CH$_2$OP), 4.2 (m, 2H, POCH$_2$) 6.65 (m, 1H, NH). Proton nuclear magnetic resonance spectra were recorded in CDCl$_3$ on either a Bruker 300-MHz or a Varian 400-MHz spectrometer. Chemical sh.ifts are reported in parts per million relative to internal tetramethylsilane. The bromoethyl phosphate intermediate was dissolved in a solution of chloroform:isopropanol:DMF (3:5:5) and trimethylamine (40% aqueous, 2 mL) was addecl. The reaction mixture was heated to 65° C. for 5 hours and then allowed to cool to room temperature before silver carbonate (90 mg) was added. Heat was reapplied for 1 hour, then the reaction mixture was cooled and filtered. Solvent was removed in vacuo and the phospholipid purified by column chromatography giving 68 mg (47%).

Alternatively, the displacement of bromide can be performed with condensed trimethylamine gas in acetone in a heated pressure flask.

EXAMPLE 3

Preparation of 2-(Hexadecylthio)ethyl phosphocholine (CP-9)

A. Preparation of 2-(Hexadecylthio)ethanol

Thioethanol (5.0 g, 64 mmol), hexadecyl bromide (25.0 g, 82 mmol), and KOH (4.5 g, 80 mmol) were combined in 95% EtOH (150 mL). The reaction mixture was stirred at room temperature overnight and then diluted with $H_2O$. The precipitate was collected and recrystallized from MeOH to provide the thioether: 19.0 g, 96%; mp 50° C.; NMR (300 MHz, $CDCl_3$) δ 0.89 (t, 3 H, $CH_3$), 1,30 (m, 26 H, $(CH_2)_{13}$), 1.60 (m, 2 H, $CH_2CH_2S$), 2.52 (t, 2 H, $SCH_2$), 2.72 (m, 2 H, $CH_2S$), 3.72 (m, 2 H, $CH_2OH$).

B. Preparation of 2-(Hexadecylthio) ethyllphoslphocholine (CP-9)

2-(Hexadecylthio)ethanol (1.0 g, 3.0 mmol) and $Et_3N$ (0.40 g, 4.0 mmol) were dissolved in anhydrous benzene (75 mL). The solution was cooled to 0° C. before a solution of 2-chloro-2-oxo-1,3,2-dioxaphospholane (0.65 g, 4.6 mmol, Fluka) in anhydrous benzene was slowly added. The reaction mixture was stirred overnight at room temperature and then filtered. The filtrate was reduced, and the residue was dissolved in $CH_3CN$ (50 ml) and transferred to a glass bomb. Condensed $N(CH_3)_3$ (2.0 g, 34 mmol) was added, and the mixture was heated at a gentle reflux for 24 h. Upon cooling of the reaction mixture, a white precipitate formed. The solid was removed and recrystallized with $Et_2O$ to provide 980 mg of 2-(Hexadecylthio)ethylphosphocholine. 70%; dec>200° C.; NMR (400 MHz, $CDCl_3$) δ 0.86 (t, 3 H, $CH_3$), 1.21 (s, 26 H, $(CH_2)_{13}$), 1.53 (m, 2 H, $CH_2CH_2S$), 2.51 (t, 2 H, $SCH_2$), 2.72 (t, 2 H, $CH_2S$), 3.37 (s, 9 H, $N(CH_3)_3$), 3.81 (m, 2 H, $CH_2N$), 3.91 (m, 2 H, $CH_2OP$), 4.31 (m, 2 H, $POCH_2$); FAB MS m/e 468 (MH+).

EXAMPLE 4

Preparation of 3'-Azido-3'-deoxy-5'-(3-dodecyloxy-2-decyloxypropyl)-phosphothymidine (CP-126)

A. Preparation of 3-Dodecyloxy-1,2-propanediol

Isopropylideneglycerol (solketal, 26.4 g, 0.20 mol) in 60 mL of toluene was added dropwise to a solution of powered KOH (22.4 g, 0.04 mol) in 150 mL of toluene. The resulting mixture was refluxed for 4 h. 1-Bromododecane (50 g, 0.20 mol) in 40 mL of toluene was then added dropwise, and the solution was refluxed for 10 h. After cooling, the reaction mixture was diluted with 200 mL of ice-water and extracted with diethyl ether (3×100 mL). The ether layers were dried over magnesium sulfate, and the solvent was removed in vacuo. The residue was dissolved in 60 mL of diethyl ether and 260 mL of MeOH. Concentrated HCl (60 mL) was added, and the solution refluxed for 16 h. After cooling, ice-water (150 mL) was addecl, and the layers separated. The aqueous layer was extracted with diethyl ether (2×75 mL). The combined organic fractions were then dried over sodium sulfate, filtered, and concentrated in vacuo. The solid residue was recrystallized from MeOH to give 37 g (0.14 mol, 71%) of a white solid.

B. Preparation of 3-Dodecyloxy-1-triphenylmethoxy-2-propanol

The diol produced in section A was tritylated with trityl chloride (59 g, 0.21 mol) in pyridine (200 mL) at 70° C. for 5 h and then at room temperature overnight. The pyridine was removed under vacuum, and the solid residue partitioned between water and $CHCl_3$. The $CHCl_3$ layer was washed with 5% HCl and water, then dried over magnesium sulfate. After removal of solvent, the product was recrystallized from hexanes:ethyl acetate (10:1) to give 19 g of pure 3-dodecyloxy-1-triphenylrmethoxy-2-propanol.

C. Preparation of 3-Dodecyloxy-2-decyloxy-1-trinhenylmethoxypropane

3-Dodecyloxy-1-triphenylmethoxy-2-propanol (13.5 g, 0.027 mol) was added dropwise to an ice-cooled suspension of sodium hydride (80%, 1.6 g, 0.054 mol) in 150 mL of tetrahyldrofuran under nitrogen. After stirring for 2 h at room temperature, heat was applied (55° C.). 1-Bromodecane (6 g, 0.027 mol) was added dropwise, and heating continued for 6 h. After cooling for 3 h, water was added slowly. Diethyl ether (2×100 mL) was added, and the solution washed with 15% sodium thiosulfite, water, and brine. After drying over sodium sulfate, the ether was removed, ard the residue chromatographed with a gradient of hexanes:ethyl acetate (100:0 to 20:1) to give 9 g (52%) of a clear liquid.

D. Preparation of 3-Dodecyloxy-2-decyloxy-1-propanol

Detritylation of 3-dodecyloxy-2-decyloxy-1-triphenylmethoxypropane was accomplished using p-toluenesulfonic acid (0.9 g) in $CHCl_3$:MeOH (72 mL:36 mL) (stirred at room temperature for 48 h, added 10% sodium bicarbonate, extracted with $CHCl_3$, dried over magnesium sulfate, and concentrated). The residue was purified by column chromatography using a gradient of hexanes: ethyl acetate (20:1 to 5:1) to give 3.5 g (63%) of pure 3-dodecyloxy-2-decyloxy-1-propanol.

E. Preparation of 3-Dodecyloxy-2-decyloxypropyl Diphenyl Phosphate

Diphenylchlorophosphate (0.7 mL, 3.4 mmol) in 10 mL of diethyl ether was cooled to 4° C. under nitrogen. 3-Dodecyloxy-2-decyloxy-1-propanol (1.0 g, 2.6 mmol) in 15 mL of pyridine and 5 mL of diethyl ether was added. The solution was warmed to room temperature, then heated to 52° C. for 3 h. It was then cooled to room temperature, diluted with 50 mL of diethyl ether, washed with water (2×25 mL), 0.5 N HCl (25 mL), and finally with water (25 mL). The organic layer was dried over sodium sulfate, filtered, and concentrated in vacuo to an oil. Chromatography with a gradient of hexanes:ethyl acetate (10:1 to 1:1) gave 980 mg (1.5 mmol, 60%) of pure product.

F. Preparation of 3-Dodecyloxy-2-decyloxypropyl Phosphate $PtO_2$ (69 mg) was placed in a Parr hydrogenation bottle. 3-Dodecyloxy-2-decyloxypropyl Diphenyl Phosphate (500 mg) in 100 mL of EtOH was then added. The reaction mixture was hydrogenated at 15 psi for 1.5 h until hydrogen uptake stopped. The reaction mixture was then filtered through Celite, and the EtOH removed in vacuo. The oil residue was dissolved in 25 mL of pyridine, concentrated in vacuo, arid dried under high vacuum to give 350 mg of pure solid phosphatidic acid.

G. Preparation of 3'-Azido-3'-deoxy-5'-(3-dodecyloxy-2-decyloxypropyl)-phosphothymidine (CP-126)

AZT (43 mg, 0.16 mmol) and 3-dodecyloxy-2-decyloxypropyl phosphate (105 mg, 0.22 mmol) were azeotrophically dried with pyridine (3×3 mL) by in vacuo removal. Dicyclohexylcarbodiimide (220 mg, 1.07 mmol) was added and the drying repeated 4 times. A final 3 mL portion of pyridine was added, and the reaction mixture stirred at room temperature in a desiccator for 4 days. Water (1 g) was added, and the mixture stirred for 4 h. The solvents were removed in vacuo, and the crude material chromatographed on 2 g of silica gel using a gradient of CHCl$_3$:MeOH (15:1 to 2:1). The product was dissolved in 11 mL of CHCl$_3$:MeOH:H$_2$O (4:6:1) and stirred with 1.5 g of Whatman preswollen microgranular cation (Na+) exchange (carboxymethyl)-cellulose resin for 1 h to obtain the sodium salt. The resin was filtered and concentrated in vacuo to give 37 mg of 3'-Azido-3'deoxy-5'(3-dodecyloxy-2-decyloxypropyl)-phosphothymidine (CP-126) (22%). FAB ms showed a [MH+Na]+ ion at 752.4350 (C$_{35}$H$_{64}$N$_5$O$_9$PNa, 1.4 ppm) and a [M+2Na]+ ion at 774.4179 (C$_{35}$H$_{63}$N$_5$O$_9$PNa$_2$, 2.0 ppm).

EXAMPLE 5

Synthesis of N-[rac-3-(hexadecylthio-2-methoxy-1-propyl]-N, N-dimethyl-N-(2-hydroxyethyl) ammonium bromide (CP-7)

Into a two neck 25 ml round bottom flask equipped with an air condenser, thermometer and stir bar, was placed 2.0 g (0.005 mol) of (±)-1-hexadecylthio-2-methoxy-3-bromopropane, 0.5 ml (0.006 mol) of N,N-dimethylaminoethanol and 15 ml of DMF. The solution was maintained at 45–50° C. for 72 hours with continuous stirring. The reaction mixture was then cooled to room temperature, 125 ml of ether was added and the solution was kept at 0° C. for 24 hours. The resulting precipitate (800 mg) was filtered and swirled with five 50 ml portions ofethertogive (±)-3-hexadecylthio-2-methoxy-N,N-dimethyl-N-β-hydroxyethyl-1-propyl ammonium bromide (32%), (mp 107–109° C.). $^1$H-NMR (CDCl$_3$): delta, 0.87 (t, 3 H, terminal methyl), 1.2–1.6[m, 28 H, (CH$_2$)$_{14}$], 2.45–3.0(m, 4 H, S—CH$_2$, CH$_2$—S), 3.48[s, 9 H, CH$_3$—O, N(CH$_3$)$_2$], 3.9–4.3 (m, 7 H. CH, CH$_2$N, N—CH$_2$—CH$_2$—OH). Anal. (C$_{24}$H$_{52}$NO$_2$SBr) C,H,N.

EXAMPLE 6

Evaluation of Akyl lipids for Anti-HBV Activit in HEP-G2 Cells

The structures of the alkyl lipids evaluated for anti-HBV activity are presented below:

where R$_1$ R$_2$, and R$_3$ are defined below for each identified compound.

| Compound | R$_1$ | R$_2$ | R$_3$ |
|---|---|---|---|
| CP-7 | SC$_{16}$H$_{33}$ | CH$_3$ | N$^+$(CH$_3$)$_2$(CH$_2$)$_2$OH |
| CP-48 | NHC(O)C$_{15}$H$_{31}$ | CH$_3$ | PC |
| CP-49 | NHC(O)C$_{15}$H$_{31}$ | CH$_3$CH$_2$ | PC |
| CP-50 | NHC(O)C$_{17}$H$_{35}$ | CH$_3$ | PC |
| CP-51 | NHC(O)C$_{17}$H$_{35}$ | CH$_3$CH$_2$ | PC |

PC = phosphocholine [OPO$_3$CH$_2$CH$_2$N$^+$(CH$_3$)$_3$]

A. Evaluation of Cytotoxicity of Alkyl Lipid Compounds

Initially, evaluations of the alkyl lipids were done to determine whether the compounds were cytotoxic to the cells at concentrations having anti-HBV activity. The assay methodology is szt forth in Korba and Germ, *Antiviral Res.*, 19, 55–70 (1992), incorporated by reference herein. Briefly, these cell cytotoxicity evaluations were done in 96-well plates seeded with HEP-G2 cell monolayers. The hepatoblastoma cell line HEP-G2 transfected with a plasmid carrying the gene that confers resistance to C418 and four 5'-3' tandem copies of the Hepatitis B virus genome was obtained from Dr. George Acs. *Proc. Natl. Acad. Sci. USA*, 84, 1005–1009 (1987). Serial concentrations of compound were added to the RPMI-1640 growth medium and the growth medium was added to the 96-well plates containing the cell monolayers. The cells were incubated for a total of nine days at 37° C. The compound-containing medium was periodically replaced. Each compound was tested at four serial concentrations in triplicate. After nine days of treatment and incubation, 0.01% neutral red dye (Sigma, Inc.) was added to the overlay medium. Cell cytotoxicity was quantitated by measuring the average A$_{510}$. Values in Table 1 represent the percentage of average A$_{510}$ values (±standard deviation) relative to nine non-treated control wells.

TABLE 1

EVALUATION OF ALKYL LIPIDS FOR CELL CYTOTOXICITY IN HEP-G2 CELLS

| | % of Control Neutral Red Dye Uptake at Indicated Compound Conc. (µM) | | | |
|---|---|---|---|---|
| Compound | 100 | 30 | 10 | 3 |
| CP-7 | 24 ± 2 | 67 ± 3 | 102 ± 6 | 98 ± 2 |
| CP-48 | 24 ± 1 | 61 ± 2 | 97 ± 1 | 102 ± 1 |
| CP-49 | 29 ± 1 | 60 ± 4 | 99 ± 4 | 99 ± 3 |
| CP-50 | 95 ± 2 | 100 ± 3 | 99 ± 2 | 97 ± 2 |
| CP-51 | 71 ± 1 | 96 ± 2 | 100 ± 4 | 101 ± 1 |
| Control 2'-3'-dideoxycytidine | 35 ± 2 | 99 ± 2 | 102 ± 1 | 100 ± 1 |
| Control No Compound | 100 ± 1 | 100 ± 2 | 100 ± 4 | |

These results indicated that at a concentration of 30 µM, compounds CP-7, CP-48, and CP-49 inhibited neutral red dye uptake by 33, 39 and 40%, respectively, compared to 0 and 4% inhibition for CP-50 and CP-51, respectively. At a concentration of 100 µM, CP-50 and CP-51 inhibited neutral red dye uptake by 5 and 29%, respectively. These data indicate that at anti-HBV concentrations of 10 µM (see Tables 2, 3, or 4), the compounds did not inhibit neutral red dye uptake. In summary, the phospholipids were not cytotoxic to the cells at concentrations that have anti-HBV activity.

B. Evaluation of Alkyl Lipids for Anti-hepatitis B Virus Activity in HEP-G2 Cells Persistently Infected with HBV HEP-G2 cells persistently infected with HBV were treated daily with fresh D-MEM containing 20% FBS and 10 µM compound. After 9 days incubation and treatment, the overlay medium was harvested to assay the quantity of Hepatitis B virus s antigen (HBsAg) and HBeAg by EIA (Abbott Laboratories). The overlay medium was diluted to levels of antigen in the linear range of the assay. Standard curves using dilutions of positive HBsAg and HBeAg controls were included in each assay. Virion DNA was assayed using the method set forth in Korba and Gerin, *Antiviral Res.*, 19, 5,5–70 (1992), incorporated by reference herein. HBV DNA was extracted from the overlay medium containing virus particles and analyzed by a slot-blot hybridization technique using $^{32}$P-labelled 3.2 Kb Eco R1 HBV DNA fragment by comparisons to HBV standards present on nitrocellulose filters using an AMBIS beta scanner. EC$_{90}$ values (90% effective concentration, i.e., drug concentration which induces a 90% decrease in the levels of HBV DNA replication intermediates in treated versus control cells) were calculated by linear regression analysis. The relative levels of HBsAg, HBeAg and virion DNA were calulated as a percentage of the average levels obtained from the untreated controls.

Results from these bioassays are shown in Table 2. These results indicate that CP-7 had moderate anti-HBV inhibitory activity and that CP-49 and CP-51 had potent inhibitory activity against HBV-induced virion DNA and HBeAg syntheses. In contrast, CP-48 and CP-50 had no significant activity against HBV induced virion DNA and HBeAg syntheses. The compounds had no significant activity against HBV induced HBsAg synthesis.

TABLE 2

EVALUATION OF ALKYL LIPIDS FOR ANTI-HEPATITIS B VIRUS ACTIVITY IN HEP-G2 CELLS PERSISTENTLY INFECTED WITH HBV

| Compound | Relative Level of HBV Antigens or Virion DNA After 9 Days Treatment (% Untreated Control) | | |
|---|---|---|---|
| (10 $\mu$M) | HBsAg | HBeAg | DNA |
| CP-7 | 74 | 43 | 10 |
| CP-48 | 73 | 88 | 96 |
| CP-49 | 115 | 30 | 1 |
| CP-50 | 104 | 93 | 88 |
| CP-51 | 99 | 28 | 2 |
| Control 2',3'-dideoxycytidine | 106 | 108 | 2 |
| Control - No Compound | 98 | 105 | 97 |

C. Evaluation of CP-51 Against HBV-Induced Antigen Syntheses

Further studies were performed to evaluate the most potent anti-HBV compound, CP-51, against HBV-induced antigen syntheses. The results from these studies are given in Table 3. The results indicate that CP-51 had no inhibitory activity against HBsAg synthesis. In contrast, CP-51 inhibited HBeAg and HBcAg syntheses by 76 and 68%, respectively. The control compound ddC had no inhibitory activity against HBV-induced antigen syntheses. In summary, these results indicate that CP-51 has selective inhibitory activity against HBeAg and HBcAg syntheses.

TABLE 3

EVALUATION OF ALKYL LIPIDS FOR ANTI-HEPATITIS B VIRUS ACTIVITY IN HEP-G2 CELLS PERSISTENTLY INFECTED WITH HBV

| Compound | Relative Levels of HBV Antigens After 9 Days Treatment (% Untreated Control) | | |
|---|---|---|---|
| (10 $\mu$M) | HBsAg | HBeAg | HBcAg |
| CP-51 | 88 | 24 | 32 |
| Control 2',3'-dideoxycytidine | 96 | 95 | 102 |
| Control - No compound | 100 | 100 | 100 |

HBsAg = HBV surface antigen
HBeAg = HBV "e" antigen
HBcAg = HBV core antigen

D. Evaluation of Effects of CP-51 on HBV-Induced DNA and RNA Synthesis

Experiments were performed to determine the effects of CP-51 on HBV induced DNA and RNA syntheses. HEP-G2 cells persistently infected with HBV were treated daily with fresh D-MEM containing 20% FBS and 10 $\mu$M compound. After 9 days incubation and treatment the cells and overlay medium were harvested separately to assay the quantity of nucleic acids. Details of the methodology of the assays are given in Section B above. Extracellular virion DNA in untreated cells ranged from 50 to 150 pg/ml in the overlay medium. Intracellular HBV DNA replication intermediates (RI) in untreated cells ranged from 50 to 100 pg/$\mu$g cell DNA. Hybridization analysis results in about 1 pg intracellular HBV DNA/$\mu$g cellular DNA to 2–3 genomic copies per cell and 1.0 pg of extracellular HBV DNA/ml overlay medium to $3 \times 10^3$ viral particles/ml. HBV RNA was analyzed by Northern blot hybridization analysis using a $^{32}$P-labeled 3.2 Kb gel-purified cloned genomic probe. Quantitive analysis of intracellular HBV DNA anc 14BV RNA was performed using an AMBIS beta scanner.

Results presented in Table 4 indicate that CP-51 inhibited virion, replication intermediates (RI) and 3.2 Kb DNA syntheses by 98, 88 and 58%, respectively. In contrast, CP-51 had no significant effects on HBV-induced RNA syntheses. The control compound ddC also inhibited HBV-induced DNA synthesis but not RNA syntheses.

TABLE 4

EVALUATION OF ALKYL LIPID CP-51 FOR ANTI-HEPATITIS B VIRUS ACTIVITY IN HEP-G2 CELLS PERSISTENTLY INFECTED WITH HBV

| Compound | Relative Levels of HBV Nucleic Acids After 9 Days Treatment (% Untreated Control) | | | | | |
|---|---|---|---|---|---|---|
| (10 $\mu$M) | Virion DNA | HBV RI | 3.2 Kb DNA | Total RNA | 3.6 Kb RNA | 2.1 Kb RNA |
| CP-51 | 2 | 12 | 42 | 112 | 84 | 112 |
| Control 2',3'-dideoxycytidine | 2 | 6 | 46 | 92 | 92 | 105 |
| Control - No Compound | 100 | 100 | 100 | 100 | 100 | 100 |

In summary, of the phospholipid compounds evaluated, CP-51 has the most potent anti-HBV activity. CP-51 is selective for inhibiting HBV-induced HBcAg, HBeAg, virion DNA and HBV RI syntheses but not HBsAg or RNA syntheses. These data also indicate that the antiviral activity of CP-51 is not due to cell cytotoxicity of the compound.

EXAMPLE 7

Evaluation of Alkyl Lipids for Anti-HBV Activity in HBV Persistently Infected Human Hepatablastoma Cell Line HEP-G2

A. Evaluation of Cytotoxicity of Alkyl Lipid Compounds

An analysis was periormed to determine the cytotoxicity of the following compounds in human HEP-G2 cells persistently infected with HBV: CP-51, CP-49, CP-9, CP-126, lyso PAF and CP-7. 2'-3'-Dideoxycytidine (ddC) was used as a control in this cytotoxicity analysis. The toxicity analyses were performed in 96-well flat bottomed tissue culture plates following the same procedure set forth in Example 6 above. Each compound was tested at four concentrations, each in triplicate cultures. Uptake of neutral red dye was used to determine the relative level of toxicity. The absorbance of internalized dye at 510 nM ($A_{510}$) was used for the quantitative analysis. The results are given in Table 5.

Values are presented as a percentage of the average $A_{510}$ values (± standard deviations) in ninz separate cultures of untreated cells maintained on the same 96-well plate as the test compounds. The percentage of dye uptake in the nine control cultures was 100±1. Cell toxicity (greater than 50% depression of the dye uptake levels observed in untreated cells) did not occur at concentrations of alkyl lipids (CP-49, CP-51, CP-7, CP-9 and CP-126) that have strong or moderate antiviral activity.

TABLE 5

CYTOTOXICITY ANALYSIS OF COMPOUNDS IN HBV PERSISTENTLY INFECTED HUMAN HEP G2 CELLS

| Trials | Compound | % of Control Neutral Red Dye Uptake At Indicated Compound Concentration (% of Control + S.D.) | | | |
|---|---|---|---|---|---|
| 1 | Control 2'-3'-Dideoxycytidine | 300 μM (34 ± 4) | 100 μM (97 ± 2) | 30 μM (100 ± 1) | 10 μM (101 ± 2) |
| 1 | Alkyl Lipid CP-51 | 100 μM (85 ± 2) | 30 μM (100 ± 3) | 10 μM (102 ± 1) | 3 μM (98 ± 3) |
| 2 | Control 2'-3'-Dideoxycytidine | 1000 μM (12 ± 5) | 300 μM (40 ± 4) | 30 μM (102 ± 2) | 10 μM (101 ± 3) |
| 2 | Alkyl Lipid CP-51 | 100 μM (44 ± 2) | 30 μM (91 ± 1) | 10 μM (98 ± 4) | 30 μM (100 ± 2) |
| 2 | Alkyl Lipid CP-49 | 100 μM (45 ± 4) | 30 μM (75 ± 1) | 10 μM (97 ± 2) | 30 μM (100 ± 1) |
| 2 | Alkyl Lipid CP-9 | 100 μM (45 ± 2) | 30 μM (86 ± 2) | 10 μM (99 ± 2) | 3 μM (100 ± 1) |
| 2 | Alkyl Lipid-AZT Conjugate CP-126 | 100 μM (20 ± 2) | 30 μM (68 ± 1) | 10 μM (97 ± 3) | 3 μM (100 ± 1) |
| 2 | Platelet Activating Factor (lyso PAF) | 100 μM (40 ± 6) | 30 μM (98 ± 2) | 10 μM (99 ± 1) | 3 μM (98 ± 2) |
| 3 | Control 2',3'-Dideoxycytidine | 300 μM (35 ± 2) | 100 μM (99 ± 2) | 30 μM (102 ± 1) | 10 μM (100 ± 1) |
| 3 | Alkyl Lipid CP-51 | 100 μM (71 ± 1) | 30 μM (96 ± 2) | 10 μM (100 ± 4) | 3 μM (101 ± 1) |
| 3 | Alkyl Lipid CP-49 | 100 μM (29 ± 1) | 30 μM (60 ± 4) | 10 μM (99 ± 4) | 3 μM (99 ± 3) |
| 3 | Nonphosphorus Alkyl Lipid (Inverse Choline) CP-7 | 100 μM (24 ± 2) | 30 μM (67 ± 3) | 10 μM (102 ± 6) | 3 μM (98 ± 2) |

B. Evaluation of Effect of Alkyl Lipids on HBV Replication

Cells were treated with a particular compound for nine days at 37° C. Analysis of intracellular HEIV DNA was done 24 hours following the ninth day of treatment. Table 6 shows the level of inhibition of HBV virion DNA and intracellular HBV DNA replication intermediates. The levels of integrated HBV DNA in each cellular DNA preparation were used to calculate the levels of episomal 3.2–3.8 Kb HBV genomes (Mono) and HBV DNA replication intermediates (RI). A zero value indicates an undetectable level of HBV virion DNA. The sensitivity cut-off was 0.1 pg DNA/ml of culture medium.

TABLE 6

EFFECT OF ALKYL LIPIDS ON HBV REPLICATION IN HBV PERSISTENTLY INFECTED HUMAN HEP G2 CELL

| Compound | Conc (μM) | Intracellular HBV DNA (pg/μg Cell DNA) | | HBV Virion DNA (pg/ml Culture Medium) | | | |
|---|---|---|---|---|---|---|---|
| | | Mono | RI | Day 0 | 3 | 6 | 9 |
| Positive Control Dideoxycytidine | 10 | 1.0 | 8 | 67 | 49 | 20 | 2 |
| | | −1.4 | 8 | 64 | 55 | 18 | 3 |
| | | 1.3 | 7 | 58 | 50 | 17 | 1 |
| | | 1.8 | 9 | 59 | 58 | 15 | 2 |
| Negative Control Untreated | 0 | 2.2 | 70 | 63 | 63 | 84 | 94 |
| | | 2.0 | 80 | 80 | 70 | 65 | 83 |
| | | 2.6 | 72 | 66 | 68 | 70 | 84 |
| | | 2.7 | 55 | 62 | 60 | 82 | 78 |
| Alkyl Lipid (CP-49) | 10 | 2.6 | 9 | 73 | 49 | 21 | 1 |
| | | 2.4 | 8 | 53 | 55 | 22 | 1 |
| | | 2.2 | 6 | 56 | 57 | 19 | 3 |
| | | 2.7 | 9 | 77 | 50 | 24 | 2 |
| | 1 | 2.3 | 24 | 56 | 56 | 38 | 10 |
| | | 2.4 | 20 | 51 | 58 | 41 | 13 |
| | | 2.2 | 25 | 66 | 60 | 43 | 11 |
| | | 2.1 | 30 | 79 | 68 | 44 | 18 |
| | 0.1 | 2.2 | 60 | 71 | 72 | 62 | 75 |
| | | 2.3 | 61 | 55 | 56 | 69 | 65 |
| | | 2.5 | 74 | 72 | 88 | 55 | 77 |
| | | 2.6 | 79 | 62 | 75 | 55 | 57 |
| Nonphosphorus Alkyl Lipid (Inverse Choline) (CP-7) $C_{24}H_{52}NO_2SBN$ N-[rac-3-(hexadecylthio)-2-methoxy-1-propyl]-N,N-dimethyl-N-(2-hydroxyethyl) | 10 | 2.3 | 11 | 49 | 70 | 35 | 8 |
| | | 2.3 | 13 | 63 | 64 | 28 | 9 |
| | | 2.6 | 10 | 70 | 67 | 33 | 7 |
| | | 2.5 | 14 | 65 | 59 | 33 | 7 |
| | 1 | 2.7 | 70 | 53 | 56 | 46 | 48 |
| | | 2.2 | 75 | 64 | 51 | 52 | 44 |
| | | 2.3 | 63 | 54 | 66 | 59 | 49 |
| | | 2.4 | 68 | 54 | 58 | 59 | 41 |
| | 0.1 | 2.5 | 73 | 51 | 72 | 58 | 57 |

TABLE 6-continued

EFFECT OF ALKYL LIPIDS ON HBV REPLICATION
IN HBV PERSISTENTLY INFECTED HUMAN HEP G2 CELL

| Compound | Conc ($\mu$M) | Intracellular HBV DNA (pg/$\mu$g Cell DNA) | | HBV Virion DNA (pg/ml Culture Medium) | | | |
|---|---|---|---|---|---|---|---|
| | | Mono | RI | Day 0 | 3 | 6 | 9 |
| ammonium | | 2.6 | 62 | 51 | 75 | 65 | 89 |
| bromide | | 2.8 | 57 | 77 | 66 | 98 | 84 |
| | | 2.3 | 76 | 64 | 51 | 75 | 76 |
| Alkyl | 10 | 2.3 | 13 | 60 | 52 | 33 | 10 |
| Lipid (CP-9) | | 2.2 | 14 | 66 | 68 | 40 | 14 |
| $C_{23}H_{50}NO_4SP$ | | 2.2 | 17 | 61 | 57 | 39 | 11 |
| 2-Hexadecylthio-1- | | 2.3 | 12 | 52 | 60 | 41 | 14 |
| ethylphosphocholine | 1 | 2.1 | 53 | 59 | 66 | 57 | 69 |
| | | 2.6 | 82 | 53 | 60 | 52 | 71 |
| | | 2.3 | 67 | 60 | 82 | 88 | 94 |
| | | 2.6 | 60 | 58 | 55 | 78 | 76 |
| | | 2.0 | 53 | 50 | 52 | 83 | 94 |
| | | 2.2 | 54 | 55 | 64 | 78 | 69 |
| | | 2.4 | 64 | 65 | 90 | 91 | 80 |
| | | 2.4 | 66 | 59 | 63 | 64 | 92 |
| Alkyl Lipid-AZT | 10 | 1.9 | 14 | 60 | 59 | 20 | 13 |
| Conjugate | | 2.5 | 9 | 62 | 50 | 21 | 8 |
| (CP-126) | | 2.0 | 12 | 59 | 55 | 26 | 9 |
| $C_{35}H_{63}N_5O_9P$ | | 2.3 | 16 | 51 | 66 | 29 | 12 |
| 3'-Azido-3'-Deoxy- | 1 | 2.3 | 51 | 67 | 49 | 40 | 28 |
| 5'-(rac-3- | | 2.7 | 67 | 54 | 57 | 39 | 20 |
| dodecyloxy- | | 2.1 | 56 | 70 | 65 | 44 | 22 |
| 2-decyloxy-1-propyl | | 1.8 | 61 | 69 | 53 | 48 | 26 |
| phosphothymidine | 0.1 | 2.2 | 64 | 50 | 77 | 61 | 78 |
| | | 2.2 | 54 | 52 | 79 | 72 | 64 |
| | | 2.6 | 70 | 54 | 67 | 83 | 82 |
| | | 2.4 | 89 | 60 | 65 | 66 | 77 |
| Platelet Activity | 10 | 2.0 | 15 | 52 | 65 | 36 | 14 |
| Factor (lyso PAF) | | 2.4 | 22 | 62 | 71 | 34 | 18 |
| $C_{26}H_{56}NO_6P$ | | 2.6 | 18 | 60 | 51 | 30 | 11 |
| rac-3-octadecyloxy- | | 2.8 | 21 | 68 | 50 | 32 | 13 |
| 2-hydroxy-1-propyl | 1 | 2.6 | 74 | 52 | 69 | 72 | 74 |
| phosphocholine | | 2.9 | 83 | 51 | 61 | 79 | 83 |
| | | 2.4 | 59 | 63 | 53 | 81 | 59 |
| | | 2.6 | 84 | 65 | 69 | 79 | 88 |
| | 0.1 | 2.5 | 84 | 62 | 77 | 80 | 84 |
| | | 2.1 | 96 | 60 | 81 | 79 | 96 |
| | | 2.0 | 67 | 81 | 70 | 64 | 67 |
| | | 2.0 | 71 | 57 | 69 | 88 | 92 |
| Alkyl Lipid | 10 | 1.7 | 4 | 59 | 55 | 20 | 2 |
| (CP-51) | | 1.9 | 3 | 58 | 49 | 13 | 2 |
| EXP 1 | | 1.8 | 5 | 60 | 44 | 10 | 1 |
| | | 2.0 | 6 | 78 | 48 | 18 | 1 |
| | 1 | 2.2 | 12 | 66 | 59 | 29 | 9 |
| | | 2.3 | 12 | 89 | 47 | 35 | 8 |
| | | 2.3 | 16 | 74 | 59 | 36 | 12 |
| | | 2.4 | 17 | 70 | 68 | 30 | 10 |
| | 0.1 | 2.7 | 63 | 58 | 58 | 79 | 83 |
| | | 2.4 | 72 | 55 | 65 | 57 | 86 |
| | | 2.3 | 84 | 60 | 68 | 81 | 76 |
| | | 2.5 | 78 | 55 | 79 | 84 | 80 |
| Alkyl | 10 | 1.3 | 7 | 51 | 33 | 12 | 0 |
| Lipid | | 1.1 | 3 | 56 | 30 | 11 | 1 |
| (CP-51) | | 1.2 | 5 | 58 | 36 | 10 | 1 |
| EXP 2 | | 1.0 | 4 | 64 | 40 | 14 | 0 |
| | 1 | 2.3 | 14 | 51 | 59 | 30 | 9 |
| | | 2.6 | 17 | 50 | 63 | 20 | 13 |
| | | 2.0 | 16 | 57 | 51 | 33 | 11 |
| | | 2.0 | 13 | 60 | 60 | 29 | 10 |
| | 0.1 | 2.7 | 78 | 52 | 69 | 78 | 38 |
| | | 2.3 | 60 | 56 | 66 | 63 | 40 |
| | | 2.9 | 54 | 43 | 66 | 68 | 40 |
| | | 2.2 | 80 | 59 | 70 | 70 | 32 |
| Alkyl | 1 | 2.2 | 17 | 92 | 110 | 32 | 14 |
| Lipid | | 2.0 | 23 | 55 | 66 | 37 | 16 |
| (CP-51) | | 2.3 | 21 | 54 | 69 | 30 | 12 |

TABLE 6-continued

EFFECT OF ALKYL LIPIDS ON HBV REPLICATION
IN HBV PERSISTENTLY INFECTED HUMAN HEP G2 CELL

| Compound | Conc ($\mu$M) | Intracellular HBV DNA (pg/$\mu$g Cell DNA) | | HBV Virion DNA (pg/ml Culture Medium) | | | |
|---|---|---|---|---|---|---|---|
| | | Mono | RI | Day 0 | 3 | 6 | 9 |
| EXP 3 | | 2.1 | 18 | 59 | 58 | 38 | 11 |
| | 0.1 | 2.4 | 40 | 75 | 79 | 78 | 110 |
| | | 2.6 | 62 | 67 | 100 | 85 | 95 |
| | | 2.1 | 81 | 57 | 66 | 58 | 64 |
| | | 2.3 | 51 | 83 | 62 | 78 | 49 |

Compounds CP-49 and CP-51 markedly inhibited the levels of HBV virion DNA and intracellular HBV $R_1$ DNA to levels comparable to, or greater than, that observed following evaluation of an internal positive control compound 2',3'-dideoxycytidine (ddC). Compounds CP-7, CP-9, and CP-126 were moderately inhibitory of HBV replication. The levels of virion DNA and HBV RI DNA were reduced to amounts comparable to, but slightly less than, the internal standard compound ddC.

C. Effect of Alkyl Lipids on Antigen Markers

Cells were treated with compound for nine days at 37° C. The overlay medium was harvested to measure levels of HBsAg, HBeAg and virion DNA. HBsAg and HBeAg were assayed by EIA (Abbott Laboratories). Virion DNA levels were measured as described in section B above. None of the compounds tested (CP-51, CP-49, CP-9, CP-7 and CP-126) affected HBV-induced hepatitis B virus surface antigen (HBsAg) levels released by persistently infected cells into the culture medium, as shown in Table 7.

TABLE 7

EFFECT OF ALKYL LIPIDS AND ALKYL LIPID-AZT
CONJUGATE ON SYNTHESIS OF ANTIGEN MARKERS IN
PERSISTENTLY INFECTED HUMAN HEP G2 CELL CULTURES

| Compound | Conc ($\mu$M) | Relative Level of HBV Antigens % of Untreated Control | | |
|---|---|---|---|---|
| | | HBsAg | HBeAg | Virion DNA |
| Untreated Control | — | 103 | 110 | 89 |
| | | 97 | 90 | 106 |
| | | 96 | 108 | 109 |
| Positive Control Dideoxycytidine (2'-3' ddC) | 10 | 100 | 101 | 2 |
| | | 112 | 115 | 2 |
| | | 102 | 98 | 2 |
| Ethanol Control @ 1% | — | 84 | 85 | 102 |
| | | 105 | 93 | 97 |
| Alkyl Lipid (CP-51) | 10 | 78 | 23 | 0 |
| | | 114 | 20 | 1 |
| Alkyl Lipid | 10 | 116 | 33 | 1 |

TABLE 7-continued

EFFECT OF ALKYL LIPIDS AND ALKYL LIPID-AZT
CONJUGATE ON SYNTHESIS OF ANTIGEN MARKERS IN
PERSISTENTLY INFECTED HUMAN HEP G2 CELL CULTURES

| Compound | Conc ($\mu$M) | Relative Level of HBV Antigens % of Untreated Control | | |
|---|---|---|---|---|
| | | HBsAg | HBeAg | Virion DNA |
| (CP-49) | | 113 | 26 | 1 |
| Alkyl Lipid (CP-9) | 10 | 68 | 53 | 13 |
| | | 64 | 57 | 16 |
| Platelet Activating Factor (lyso PAF) | 10 | 78 | 45 | 13 |
| | | 80 | 50 | 15 |
| Nonphosphorus Alkyl Lipid Inverse Choline (CP-7) | 10 | 79 | 46 | 9 |
| | | 69 | 40 | 10 |
| Lipid-AZT Conjugate (CP-126) | 10 | 65 | 35 | 10 |
| | | 69 | 42 | 14 |

In contrast, the active antiviral compounds (CP-51, CP-49, CP-9, lyso PAF, CP-7, and CP-126) all caused a reduction in Hepatitis B virus e antigen (HBeAg) and virion DNA levels. The most active compounds in suppressing HBeAg and virion DNA levels were CP-51 and CP-49. These data suggest that the anti-HBV alkyl lipids and alkyl lipid-AZT conjugate act in a similar manner.

Further analyses were carried out with compound CP-51. Again, the cells were treated for nine days at 37° C. The overlay medium was harvested to measure levels of HBsAg, HBeAg, HBcAg, virion DNA, RI DNA and RNA levels. HBsAg and HBeAg were assayed by EIA (Abbott Laboratories). HBcAg was assayed by a solid phase EIA. HBV RNA was analyzed by Northern blot hybridization using a $^{32}$P-labelled 3.2 Kb genomic probe. Intracellular HBV RNA and RI HBV DNA was quantitated using a AMBIS beta scanner. The results are given in Table 8.

TABLE 8

EFFECT OF ALKYL LIPID ON HBV INDUCTION
OF ANTIGEN MARKERS, DNA AND RNA IN PERSISTENTLY
INFECTED HUMAN HEP-G2 CELL CULTURES

Relative Level of Antigen Markers, DNA and RNA

| Compound | Conc ($\mu$M) | HBsAg | HBeAg | HBcAg | Virion DNA | Intra-cellular HBV-DNA | RI DNA | 3.2 Kb RNA | Total RNA | 3.6 Kb RNA |
|---|---|---|---|---|---|---|---|---|---|---|
| Untreated Controls | — | 100 | 100 | 100 | 100 | 100 | 100 | 100 | 100 | 100 |
| Positive Control Dideoxycytidine (2'-3'-ddC) | 10 | 96 | 95 | 102 | 2 | 6 | 46 | 92 | 92 | 105 |
| Alkyl Lipid (CP-51) | 10 | 88 | 24 | 32 | 2 | 12 | 42 | 112 | 84 | 112 |

Results of these analyses indicated that CP-51 did not significantly alter the level or size of HBV induced RNA transcripts of HBsAg. These results suggest that CP-51 does not affect HBV transcription or production of HBsAg. In addition to CP-51 inhibiting RI HBV-DNA and virion DNA formation, as seen in Tables 6 and 8, the alkyl lipid significantly inhibited the levels of Hepatitis B core antigen (HBcAg), as seen in Table 8. Because both HBeAg and HBcAg are inhibited by CP-51, it appears that the mechanism of action of the compound involves suppression of nucleocapsid and HBV pregenomic RNA packaging to form infectious HBV particles. HBeAg is a known proteolytic product of HBcAg, which would account for inhibition of these HBV antigens by CP-51. Inhibition of these essential viral antigens would cause a downstream effect on the inhibition of intracellular RI HBV DNA and formation of packaged virion DNA.

EXAMPLE 8

In Vivo Evaluatiori of CP-51 for Cytotoxicity and Bioavailability

A. Biologic Activity of CP-51

Figure 1:
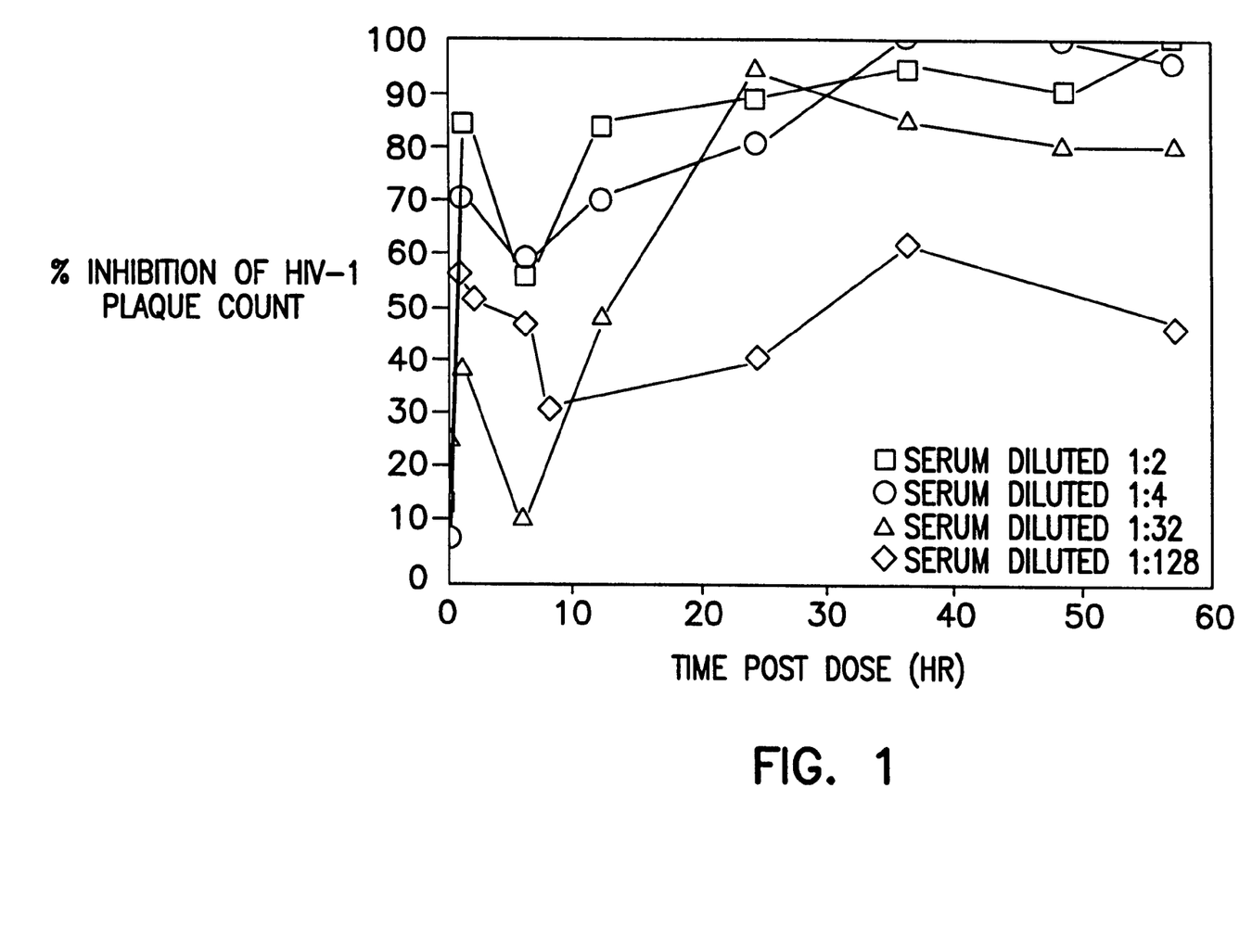
FIG. 1 depicts biological activity of the alkyl lipid CP-51 in rat serum after a single oral dose of the compound was administered to Sprague Dawley rats.

The biologic activity of alkyl lipid CP-51 was evaluated in vivo. Sprague Dawley rats were fasted for 18 hours and received a single oral dose of 15 mg/kg of the alkyl lipid CP-51 by gavage. An in-dwelling carotid catheter was used to harvest whole blood at various times post-dose. The plasma containing the alkyl lipid was diluted 1:2 to 1:128 in phosphate buffered saline and assayed for biologic activity using the HIV-1 syncytial plaque test. CEM-SS cell monolayers were infected with HIV-1 and overlaid with RPMI-1640 medium containing serial dilutions of plasma. After incubation for five days at 37° C., the number of HIV-1 syncytial plaques was counted as previously described (Kucera et al., *AIDS Res. Human Retroviruses*, 6: 491–501, (1990)). The data in FIG. 1 indicate that CP-51 is rapidly absorbed into the blood of rats following a single oral dose of 15 mg/kg by gavage. The data also indicate that biologically active concentrations of the compound CP-51 were obtained in the blood (plasma).

B. Cytotoxicity Assay

CP-51 and AZT were assayed for cytotoxicity by inhibition of mouse precursor erythrocyte (CFU-E) and granulocyte/macrophage (CFU-GM) cell colony formation. Mouse bone marrow precursor cells were suspended in soft-agar-RPMI-1640 medium supplmented with cell growth factors and serial concentrations of alkyl lipid. After incubation at 37° C. to allow cell colony formation, the number of colony-forming units in the presence and absence of alkyl lipid was calculated to determine the inhibitory concentration for 50% ($IC_{50}$). The inhibitory concentration 50% ($IC_{50}$) for CP-51 was 41 microgram/ml (CFU-E) and 11 microgram/ml (CFU-GM) compared to 0.43 microgram/ml (CFU-E) and 0.27 microgram/ml (CFU-GM) for AZT. These results indicated that CP-51 was significantly less cytotoxic than AZT.

C. Inhibition of Reirovirus-Induced Splenomepaly

Mice were infected I.P. with Friend-Leukemia virus and not treated or treated I.P. with daily doses of phospholipid. After 14 days infection and treatment, the mice were sacrificed, the spleens were removed and weighed to determine the percentage, of control splenomegaly. As indicated in Table 9, CP-51 inhibited retrovirus-induced splenomegaly 43% in mice receiving a dose of 12.5 mg/kg/day intra peritoneally compared to 10% inhibition by the same dose of AZT. Even a single dose of 25 mg/kg CP-51 inhibited splenomegaly by 36%. These data indicate that CP-51 has anti-retrovirus activity in infected animals.

TABLE 9

Effect of Alkyl Lipid in Retrovirus
(Friend-Leukemia Virus) Infected Mice

| Compound | Dose (mg/kg/day) | Spleen Wt (g) (day + 14) | % of Control Splenomegaly |
|---|---|---|---|
| Virus Control | — | 2.091 ± 0.113 (4)[a] | 100 |
| CP-51 | 12.5[b] | 0.891[c] ± 0.393 (4) | 43 |
| CP-51 | 25[d] | 0.761[c] ± 0.358 (4) | 36 |
| AZT | 12.5[b] | 0.219[e] ± 0.028 (5) | 10 |

[a]Number of animals tested
[b]Daily treatment, day 0 (+ 1 hour) - day + 13; sacrifice day + 14
[c]$p \leq 0.05$ U-test
[d]One treatment, day 0 (+ 1 hour); sacrifice day + 14
[e]$p \leq 0.01$ U-test All patents, patert documents and publications are incorporated by reference herein. The foregoing examples are illustrative of the present invention, and are not to be construed as limiting thereof. The invention is defined by the following claims, with equivalents of the claims to be included therein.

That which is claimed is:

1. A method of inhibiting the production of hepatitis virus-induced antigens in a human subject, said method comprising administering an antigen inhibiting amount of a compound of Formula I:

(I)

wherein
Y is S, O, NH, $NCH_3$, NHC(O), or $NCH_3C(O)$;
$R_1$ is unbranched or branched, saturated or unsaturated C1–C20 alkyl, alkenyl, or alkynyl;
X is a covalent bond or methylene optionally substituted with hydroxyl, C1–C20 alkyl, C1–C20 alkoxy, C1–C20 alkylthio or C1–C20 alkylamido;
and D is selected from the group consisting of Formula V and Formula VI;
wherein Formula V is (V)

wherein E is selected from the group consisting of:

wherein J is C1–C4 alkyl optionally substituted one to three times with methyl or ethyl; and $R_2$, $R_3$, and $R_4$ are independently selected from the group consisting of H and C1–C3 alkyl; and
a nucleic acid base conjugate of the Formula VII (VII)

wherein the base is selected from the group consisting of thymine, adenine, cytosine, guaninie, hypoxanthine, uracil, 2'-3'-dideoxy-3'-thiacytidine, and 2-aminoadenine; A is H, fluorine, or $N_3$; and B is H or fluorine, or A and B together form a covalent bond;
and wherein Formula VI is (VI)

wherein $R_5$ and $R_6$ are independently selected from the group consisting of H and C1–C3 alkyl;
J is as defined above;
W is —OH, or —SH; and
$Z^-$ is an anion;
or a pharmaceutical salt thereof.

2. A method according, to claim 1, wherein Y is NHC(O).

3. A method according to claim 1, wherein $R_1$ is unbranched saturated or unsaturated (C1–C20 alkyl.

4. A method according to claim 1, wherein X is methylene substituted with hydroxyl or C1–C4 alkoxy.

5. A method according to claim 1, wherein X is methylene substituted with hydroxyl or C1–C4 alkoxy, Y is NHC(O), and $R_1$ is C14–C18 alkyl.

6. A method according to claim 1, wherein X is methylene substituted with hydroxyl or C1–C4 alkoxy, Y is S, and $R_1$ is C14–C18 alkyl.

7. A method according to claim 1, wherein X is a covalent bond, Y is S, and $R_1$ is C14–C18 alkyl.

8. A method according to claim 1, wherein the hepatitis virus is selected from the group consisting of Hepatitis A Virus, Hepatitis B Virus, Hepatitis C Virus, Hepatitis D Virus and Hepatitis E Virus.

9. A method according to claim 8, wherein the hepatitis virus is Hepatitis B Virus.

10. A method according to claim 9, wherein the hepatitis virus-induced antigen is selected from the group consisting of core antigen and e antigen.

11. A method of inhibiting the production of hepatitis virus-induced antigens in a human subject, said method comprising administering an antigen-inhibiting amount of a compound of Formula II:

(II)

wherein Y is S, O, NH, $NCH_3$, NHC(O), or $NCH_3C(O)$; $R_1$ is an unbranched or branched, saturated or unsaturated C1–C20 alkyl, alkenyl, or alkynyl; X is a covalent bond or methylene optionally substituted with hydroxyl, C1–C20 alkyl, C1–C20 alkoxy, C1–C20 alkylthio or C1–C20 alkylamido; J is $C_1$–$C_4$ alkyl optionally substituted 1 to 3 times with methyl or ethyl, and $R_2$, $R_3$ and $R_4$ are independently selected from the group consisting of H and C1–C3 alkyl, or a pharmaceutical salt thereof.

12. A method according to claim 11, wherein J is unsubstituted ethylene, and wherein $R_2$, $R_3$, and $R_4$ are each methyl.

13. A method according to claim 11, wherein Y is NHC(O).

14. A method according to claim 11, wherein $R_1$ is unbranched saturated or unsaturated C1–C20 alkyl.

15. A method according to claim 11, wherein X is methylene substituted with hydroxyl or C1–C4 alkoxy.

16. A method according to claim 12, wherein X is methylene substituted with hydroxyl or C1–C4 alkoxy, Y is NHC(O), and $R_1$ is C14–C18 alkyl.

17. A method according to claim 12, wherein X is methylene substituted with hydroxyl or C1–C4 alkoxy, Y is S, and $R_1$ is C14–C18 alkyl.

18. A method according to claim 12, wherein X is a covalent bond, Y is S, and $R_1$ is C14–C18 alkyl.

19. A method according to claim 12, wherein the hepatitis antigen inhibiting compound of Formula II is selected from the group consisting of rac-3-octadecanamido-2-ethyoxy-1-propylphosphocholine, rac-3-hexadecanamido-2-ethoxy-1-propylphosphocholine, 2-hexadecylthio-1-ethylphosphocholine, and rac-3-octadecyloxy-2-hydroxy-1-propyl phosphocholine.

20. A method according to claim 11, wherein the hepatitis virus is selected from the group consisting of Hepatitis A Virus, Hepatitis B Virus, Hepatitis C Virus, Hepatitis D Virus and Hepatitis E Virus.

21. A method according to claim 19, wherein the hepatitis virus is Hepatitis B Virus.

22. A method according to claim 21, wherein the hepatitis virus-induced antigen is selected from the group consisting of core antigen and e antigen.

23. A method of inhibiting the production of hepatitis virus-induced antigens in a human subject, said method comprising administering an antigen inhibiting amount of a compound of Formula III:

$$\begin{array}{c} CH_2\text{—}Y\text{—}R_1 \\ | \\ X \quad R_2 \\ | \quad | \\ CH_2\text{—}N^+\text{—}J\text{—}WZ^- \\ | \\ R_3 \end{array} \quad (III)$$

wherein Y is S, O, NH, NCH$_3$, NHC(O), or NCH$_3$C(O); R$_1$ is an unbranched or branched, saturated or unsaturated C1–C20 alkyl, alkenyl, or alkynyl; X is a covalent bond or methylenie optionally substituted 1 or 2 times with hydroxyl, C1–C20 alkyl, C1–C20 alkoxy, C1–C20 alkylthio or C1–C20 alkylamido; J is C1–C$_4$ alkyl optionally substituted 1 to 3 times with methyl or ethyl; R$_2$ and R$_3$ are independently selected from the group consisting of H and C1–C3 alkyl; and W is —OH or —SH.

24. A method according to claim 23, J is ethylene, and wherein R$_2$, and R$_3$ are each methyl.

25. A method according to claim 23, wherein Y is S and R$_1$ is unbranched saturated or unsaturated C1–C20 alkyl.

26. A method according to claim 23, wherein X is methylene substituted with methoxy or ethoxy.

27. A method according to claim 23, wherein Z$^-$ is halogen.

28. A method according to claim 24, wherein R$_1$ is C14–C18 unbranched saturated or unsaturated alkyl, Y is S, X is methylene substituted with methoxy or ethoxy, and W is —OH.

29. A method according to claim 23 wherein the hepatitis antigen inhibiting compound of formula III is N-[rac-3-(hexadecylthio)-2-methoxy-1-propyl]-N, N-dimethyl-N-(2-hydroxyethyl) ammonium bromide.

30. A method according to claim 23, wherein the hepatitis virus is selected from the group consisting of Hepatitis A Virus, Hepatitis B Virus, Hepatitis C Virus, Hepatitis D Virus and Hepatitis E Virus.

31. A method according to claim 30, wherein the hepatitis virus is Hepatitis B Virus.

32. A method according to claim 31, wherein the hepatitis virus-induced antigen is selected from the group consisting of core antigen and e antigen.

33. A method of inhibiting the production of hepatitis virus-induced antigens in a human subject, said method comprising administering an antigen inhibiting amount of a compound of Formula IV:

$$\begin{array}{c} CH_2\text{—}Y\text{—}R_1 \\ | \\ X \quad O \\ | \quad \| \\ CH_2\text{—}O\text{—}P\text{—}O\text{—}CH_2 \quad Base \\ | \\ O^- \\ \\ A \quad B \end{array} \quad (IV)$$

wherein Y is S, O, NH, NCH$_3$, NHC(O), or NCH$_3$C(O); R$_1$ is an unbranched or branched, saturated or unsaturated C1–C20 alkyl, alkenyl, or alkynyl; X is a covalent bond or methylene optionally substituted with hydroxyl, C1–C20 alkyl, C1–C20 alkoxy, C1–C20 alkyltlio or C1–C20 alkylamido; Base is selected from the group consisting of thymine, adenine, cytosine, guanine, hypoxanthine, uracil, 2'-3'-dideoxy-3'-thiacytidirie and 2-aminoadenine; A is H, fluorine, or N$_3$; and B is H or fluorine or A and B together form a covalent bond.

34. A method according to claim 33, wherein A is H or N$_3$ and B is H.

35. A method according to claim 33, wherein Y is NHC(O).

36. A method according to claim 33, wherein R$_1$ is unbranched saturated or unsaturated C1–C20 alkyl.

37. A method according to claim 33, wherein X is methylene substituted with hydroxyl or C1–C4 alkoxy.

38. A method according to claim 34, wherein X is methylene substituted with hydroxyl or C1–C4 alkoxy, Y is NHC(O), and R$_1$ is C14–C18 alkyl.

39. A method according to claim 34, wherein X is methylene substituted with hydroxyl or C1–C4 alkoxy, Y is S, and R$_1$ is C14–C18 alky.

40. A method according to claim 34, wherein X is a covalent bond, Y is S, and R$_1$ is C14–C18 alkyl.

41. A method according to claim 33, wherein the hepatitis B antigen inhibiting compound is 3'-Azido-3'-deoxy-5'-(rac-3-dodecyloxy-2-decyloxy-1-propyl) phosphothymidine.

42. A method according to claim 33, wherein the hepatitis virus is selected from the group consisting of Hepatitis A Virus, Hepatitis B Virus, Hepatitis C Virus, Hepatitis D Virus and Hepatitis E Virus.

43. A method according to claim 42, wherein the hepatitis virus is Hepatitis B Virus.

44. A method according to claim 43, wherein the hepatitis virus-induced antigen is selected from the group consisting of core antigen and e antigen.

* * * * *